United States Patent
Kreuzer et al.

(10) Patent No.: US 11,938,008 B2
(45) Date of Patent: Mar. 26, 2024

(54) ABSORBENT PANT HAVING AN ABSORBENT CORE WITH CONTINUOUS CHANNEL

(71) Applicant: The Procter & Gamble Company, Cincinnati, OH (US)

(72) Inventors: Carsten Heinrich Kreuzer, Hoffheim (DE); Ernesto Gabriel Bianchi, Hessen (DE); Bruno Johannes Ehrnsperger, Bad Soden (DE); Ling Tong, Beijing (CN); Claus Peter Stoelzel, Bad Soden (DE)

(73) Assignee: The Procter & Gamble Company, Cincinnati, OH (US)

( * ) Notice: Subject to any disclaimer, the term of this patent is extended or adjusted under 35 U.S.C. 154(b) by 926 days.

(21) Appl. No.: 16/927,027

(22) Filed: Jul. 13, 2020

(65) Prior Publication Data

US 2020/0390615 A1    Dec. 17, 2020

Related U.S. Application Data

(63) Continuation of application No. PCT/CN2018/084171, filed on Apr. 24, 2018.

(51) Int. Cl.
| | | |
|---|---|---|
| *A61F 13/494* | (2006.01) | |
| *A61F 13/49* | (2006.01) | |
| *A61F 13/496* | (2006.01) | |
| *A61F 13/53* | (2006.01) | |

(52) U.S. Cl.
CPC .. *A61F 13/49473* (2013.01); *A61F 13/49011* (2013.01); *A61F 13/4906* (2013.01); *A61F 13/49061* (2013.01); *A61F 13/4963* (2013.01); *A61F 2013/530481* (2013.01)

(58) Field of Classification Search
CPC .............. A61F 13/4756; A61F 13/4751; A61F 13/475; A61F 13/49406; A61F 13/49473; A61F 13/49001; A61F 13/49061; A61F 13/4704; A61F 13/533; A61F 13/536
See application file for complete search history.

(56) References Cited

U.S. PATENT DOCUMENTS

| | | |
|---|---|---|
| 4,854,984 A | 8/1989 | Ball |
| 4,919,738 A | 4/1990 | Ball et al. |
| 5,340,648 A | 8/1994 | Rollins |
| 5,501,756 A | 3/1996 | Rollins |

(Continued)

FOREIGN PATENT DOCUMENTS

| | | |
|---|---|---|
| CN | 104780885 A | 7/2015 |
| CN | 104837453 A | 8/2015 |

(Continued)

OTHER PUBLICATIONS

All Office Actions; U.S. Appl. No. 16/927,048.

(Continued)

*Primary Examiner* — Leslie A Lopez
*Assistant Examiner* — Seth Han
(74) *Attorney, Agent, or Firm* — Charles R. Matson

(57) ABSTRACT

The invention relates to a disposable absorbent pant comprising a central chassis and elasticized front and rear belt. The central chassis comprises an absorbent core with an absorbent layer. The absorbent layer comprises a continuous channel formed therein.

19 Claims, 17 Drawing Sheets

(56) References Cited

U.S. PATENT DOCUMENTS

| | | | |
|---|---|---|---|
| 5,507,909 | A | 4/1996 | Rollins |
| 5,700,254 | A | 12/1997 | McDowall et al. |
| 6,077,375 | A | 6/2000 | Kwok |
| 6,200,635 | B1 | 3/2001 | Kwok |
| 6,235,137 | B1 | 5/2001 | Van Eperen et al. |
| 6,361,634 | B1 | 3/2002 | White |
| 6,520,237 | B1 | 2/2003 | Bolyard, Jr |
| 6,561,430 | B2 | 5/2003 | Ou |
| 6,582,518 | B2 | 6/2003 | Riney |
| 6,610,161 | B2 | 8/2003 | Erdman |
| 6,613,146 | B2 | 9/2003 | Bolyard, Jr. |
| 6,652,693 | B2 | 11/2003 | Burriss |
| 6,719,846 | B2 | 4/2004 | Nakamura |
| 6,737,102 | B1 | 5/2004 | Saidman |
| 7,786,341 | B2 | 8/2010 | Schneider et al. |
| 8,979,815 | B2 | 3/2015 | Roe |
| 2003/0105190 | A1 | 6/2003 | Diehl et al. |
| 2009/0043275 | A1* | 2/2009 | Perneborn ............ A61F 13/56 156/162 |
| 2010/0040826 | A1 | 2/2010 | Mansfield |
| 2011/0319851 | A1* | 12/2011 | Kudo ................ A61F 13/4704 604/380 |
| 2012/0316526 | A1 | 12/2012 | Rosati et al. |
| 2012/0316528 | A1 | 12/2012 | Kreuzer |
| 2013/0211355 | A1 | 8/2013 | Nishikawa |
| 2014/0163500 | A1 | 6/2014 | Roe |
| 2014/0163501 | A1 | 6/2014 | Ehrnsperger |
| 2014/0163503 | A1 | 6/2014 | Arizti |
| 2014/0163509 | A1* | 6/2014 | Gassner ............ A61F 13/49061 604/385.16 |
| 2014/0163511 | A1 | 6/2014 | Roe et al. |
| 2014/0171898 | A1* | 6/2014 | Greening, II ......... A61F 13/505 604/385.101 |
| 2014/0358106 | A1* | 12/2014 | Tan .................... A61F 13/4752 604/385.01 |
| 2014/0371701 | A1 | 12/2014 | Bianchi |
| 2015/0045756 | A1* | 2/2015 | Wright .................... B01J 20/26 156/73.6 |
| 2015/0080839 | A1 | 3/2015 | Trapp et al. |
| 2015/0173967 | A1 | 6/2015 | Kreuzer |
| 2015/0173977 | A1 | 6/2015 | Stelzig et al. |
| 2016/0030256 | A1 | 2/2016 | Kreuzer et al. |
| 2016/0206482 | A1 | 7/2016 | Nishikawa et al. |
| 2016/0235594 | A1 | 8/2016 | Ehmsperger et al. |
| 2016/0235602 | A1* | 8/2016 | Ehrnsperger ............ A61F 13/49 |
| 2016/0354260 | A1 | 12/2016 | Roe et al. |
| 2017/0079853 | A1 | 3/2017 | Willhaus et al. |
| 2017/0312147 | A1 | 11/2017 | Bianchi |
| 2018/0021187 | A1 | 1/2018 | Nishikawa et al. |
| 2021/0030602 | A1 | 2/2021 | Kreuzer et al. |

FOREIGN PATENT DOCUMENTS

| | | |
|---|---|---|
| CN | 104853704 A | 8/2015 |
| CN | 105473113 A | 4/2016 |
| CN | 105530902 A | 4/2016 |
| CN | 105579008 A | 5/2016 |
| CN | 106535845 A | 3/2017 |
| EP | 0149880 A2 | 7/1985 |
| EP | 1447067 A1 | 8/2004 |
| EP | 1621167 A2 | 2/2006 |
| EP | 2497451 A1 | 9/2012 |
| EP | 2238953 B1 | 6/2013 |
| EP | 1913914 B2 | 8/2014 |
| JP | 2010284418 A | 12/2010 |
| JP | 2011072650 A | 4/2011 |
| JP | 2016187474 | 3/2015 |
| JP | 2016116860 A | 6/2016 |
| JP | 2018015216 A | 2/2018 |
| JP | 2018505717 A | 3/2018 |
| WO | WO9510996 | 4/1995 |
| WO | 9827908 A1 | 7/1998 |
| WO | WO200059430 A1 | 10/2000 |
| WO | WO02067809 A2 | 9/2002 |
| WO | WO2007046052 | 4/2007 |
| WO | WO2007047598 | 4/2007 |
| WO | WO2008155699 A1 | 12/2008 |
| WO | WO2009155264 | 12/2009 |
| WO | WO2009155265 | 12/2009 |
| WO | 2015031225 A1 | 3/2015 |

OTHER PUBLICATIONS

Supplementary Search Report; Application Ser. No. PCT/CN2018/084171; dated Jul. 10, 2020, 8 pages.

International Search Report and Written Opinion, PCT/CN2018/084171, dated Jan. 30, 2019.

International Search Report and Written Opinion, PCT/CN2018/084173, dated Jan. 22, 2019.

* cited by examiner

ABSORBENT PANT HAVING AN ABSORBENT CORE WITH CONTINUOUS CHANNEL

CROSS REFERENCE TO RELATED APPLICATION

This application is a continuation of Application No. PCT/CN2018/084171, filed on Apr. 24, 2018, which is incorporated herein by reference.

BACKGROUND OF THE INVENTION

Absorbent pants are well known and widely used, both for babies and infants as well as for adult incontinence. A particular type of absorbent pant design currently marketed is sometimes called the "balloon" pant. The balloon pant design usually includes a central absorbent chassis, including the absorbent core, and an elastic belt. The elastic belt is usually relatively wide (in the longitudinal direction) and elastically stretchable in the lateral direction. It entirely encircles the wearer's waist. The belt is often formed of two layers of nonwoven web sandwiching one or more elastic members, such as a plurality of laterally-oriented strands or strips of elastomeric material, or a section of elastomeric film, elastomeric scrim or elastomeric nonwoven. It is common among such designs that, in manufacture, the elastic member(s) are sandwiched between the nonwoven web layers while in a strained condition.

The absorbent core that is part of the central chassis plays an important role in containment and absorbency of exudates, as well as in comfort, fit and appearance of the pant when worn. In recent years, absorbent core designs for both absorbent pants and taped absorbent diapers have progressed toward structures with relatively higher proportions by weight of superabsorbent polymer particles and lower proportions of cellulose fibers (which are sometimes also referred to as "pulp" or "airfelt"), resulting in structures that are thinner than absorbent core designs of earlier years and enabling manufacture of products that are less bulky and more closely-fitting (e.g., more underwear-like) when dry. The latter absorbent core designs, however, can be slower in liquid acquisition rate, and because of their greater proportions of absorbent polymer particles, can become saggy, bulky and gelatinous when wetted. To address these issues, absorbent cores including longitudinally-oriented portions have been developed. Appropriately located and structured longitudinal portions can help distribute liquid along deposits of absorbent polymer particles along the length of the absorbent core, and thereby help improve acquisition rate. They also can help reduce the likelihood of a saggy and bulky appearance of the article when wetted, by providing longitudinal structural rigidity through the crotch region of the article resulting from pressure within the wetted absorbent polymer particle deposits between the portions.

It has now been found, however, that absorbent cores provided with longitudinally extending portions which work well for taped diapers, can provide certain disadvantages when being used in absorbent pants. Hence, there remains to be room for improvement regarding absorbent core designs having one or more portions which are especially beneficial for use in absorbent pants.

SUMMARY OF THE INVENTION

Upon investigation, the inventors have found that one of the disadvantages that can arise with absorbent cores having longitudinally extending channels is closely associated with the difference in the way a taped diaper is applied onto a wearer versus the way in which an absorbent pant is applied. A taped diaper is normally applied by laying the wearer on the inner surface of the rear waist region of the diaper and pulling the front waist region up over the wearer's belly such that the crotch region of the absorbent article is placed between the wearer's legs. In contrast, an absorbent pant is typically applied by having the wearer's feed and legs sliding through the leg openings of the pant and pulling the pant upwards such that the front and rear waist regions of the pant lie against the belly and the back of the wearer with the crotch portion of the pant positioned between the legs of the wearer.

If the absorbent core has longitudinally extending channels, the absorbent article tends to fold along these channels. Due to pulling the absorbent pant upwards between the wearer's legs, the absorbent core is "squeezed" between the legs of the wearer while being pulled. As a consequence, an absorbent core having longitudinally extending channels typically forms a U-shape with the edges of the absorbent core adjacent to the legs of the wearer being folded upwardly and, to some extend also somewhat inwardly. Due to the U-shape, the absorbent core may not fit optimally between the legs of the wearer, providing reduced surface which is in close contact with the body of the wearer in the crotch. The folding tends to continue to the regions outside the crotch and towards the front and rear waist region, leading to a narrowed absorbent core in these regions as well and reduced contact of the absorbent core with the body of the wearer. This may increase the risk of leakage during use. It also leads to reduced body surface coverage especially over the buttocks of the wearer.

The present invention thus provides an absorbent core having an improved channel configuration which is especially suitable for pant-type absorbent articles.

The invention relates to a disposable absorbent pant, having a longitudinal axis, a lateral axis, a front waist region, a rear waist region and a crotch region between the front and rear waist regions.

The pant comprises a central chassis extending from the front waist region through the crotch region to the rear waist region. The central chassis comprises a topsheet, a backsheet and an absorbent core placed in between the topsheet and the backsheet, the central chassis having a laterally extending chassis front edge, a laterally extending chassis rear edge and first and second longitudinally extending chassis side edges.

An elasticized front belt is provided in the front waist region and an elasticized rear belt provided in the rear waist region, the front and rear belt each having a body-facing surface and a garment-facing surface. The front belt having a transversally extending front waist edge, the rear belt having a transversally extending rear waist edge, the front and rear belt each having a first and second longitudinally extending side edge, with the first side edge of the front belt being joined to the first side edge of the rear belt and the second side edge of the front belt being joined to the second side edge of the rear belt at side seams to form a waist opening and two leg openings.

The absorbent core comprises an absorbent layer, the absorbent layer having a laterally extending front edge, a laterally extending rear edge and first and second longitudinally extending side edges. The absorbent layer comprises a continuous channel having a first and a second longitudinally-oriented elongate portion and a third and fourth laterally-oriented elongate portion.

The first portion of the continuous channel is provided between the longitudinal axis and the first side edge of the absorbent layer, the second portion is provided between the longitudinal axis and the second side edge of the absorbent layer.

The first and second portion each have a front end towards the absorbent layer's front edge, a rear end towards the absorbent layer's rear edge and a center which is equally spaced from the respective portion's front and rear ends across the longitudinal axis, each of the first and second portion being curved such that the first and second portion are closer to the longitudinal axis at a location (herein after referred to as "necking point") between the front end and the rear end of the respective first and second portion than the portion's front and rear ends.

The necking point may be located between the center and the rear end of the respective first and second portion. The necking point of the first portion may be spaced from 5% to 30%, or from 5% to 25%, or from 10% to 25% away from the center of the first portion towards the rear end, based on the total length of the first portion, as measured along a straight line from the front end to the rear end of the first portion.

Likewise, the necking point of the second portion may be spaced from 5% to 30%, or from 5% to 25%, or from 10% to 25% away from the center of the second portion towards the rear end, based on the total length of the second portion, as measured along a straight line from the front end to the rear end of the second portion.

The first and second portion may not be closer to the longitudinal axis at any other location than at their necking point.

The third portion of the continuous channel connects the front end of the first portion with the front end of the second portion and extends from the front end of the first portion to the front end of the second portion.

The fourth portion of the continuous channel connects the rear end of the first portion with the rear end of the second portion and extends from the rear end of the first portion to the rear end of the second portion.

The first portion may follow a first curved path with only one curve between the necking point and the rear end of the first portion. The first portion may follow a second curved path with only one curve between the necking point and the front end of the first portion. The first curved path of the first portion may have a steeper curvature compared to the second curved path of the first portion. The first and the second curved path of each of the first and second portion are concavely shaped relative to the longitudinal axis. This is also reflected in the Figures.

Likewise, the second portion may follow a first curved path with only one curve between the necking point and the rear end of the second portion. The second portion may follow a second curved path with only one curve between the necking point and the front end of the second portion. The first curved path of the second portion may have a steeper curvature compared to the second curved path of the second portion.

One or both of the third and fourth portion may be concavely curved (as exemplarily shown in the Figures), convexly curved, or be straight.

The first and second portion are spaced apart from each other at their necking point by a first distance L1. the absorbent layer has a first transverse width W1 measured from the first longitudinally extending side edge to the second longitudinally extending side edge of the absorbent layer across the necking point of the first and second portion. The distance L1 is from 20 mm to 50 mm, or from 25 mm to 45 mm, or from 30 mm to 45 mm, or from 35 mm to 45 mm.

The first and second portion are spaced apart from each other at their rear ends by a second distance L2. The absorbent layer has a second transverse width W2 measured from the first longitudinally extending side edge to the second longitudinally extending side edge of the absorbent layer across the rear ends of the first and second portion. The ratio of W2 to L2 is from 1.5 to 2.8, or from 1.8 to 2.5.

The ratio of W1 to L1 is higher than the ratio of W2 to L2.

The ratio of L2 to L1 is from 1.2 to 2.5, or from 1.4 to 2.2, or from 1.5 to 2.0.

The first and second portion may be spaced apart from each other at their front ends by a third distance L3. The absorbent layer has a third transverse width W3 measured from the first longitudinally extending side edge to the second longitudinally extending side edge of the absorbent layer across the front ends of the first and second portion. The ratio of W3 to L3 may be from 1.5 to 2.8, or from 1.8 to 2.5.

The ratio of W1 to L1 may be higher than the ratio of W3 to L3.

The ratio of L3 to L1 may be from 1.2 to 2.5, or from 1.4 to 2.2, or from 1.5 to 2.0.

The ratio of W1 to L1 may be from 2.5 to 4.5, or from 2.8 to 4.0, or from 3.0 to 3.8.

L2 may be the same as L3. Alternatively, L2 and L3 may not differ from each other by more than 30%, or not more than 20%, or not more than 10%, or not more than 5% based on the longer distance.

The third distance L3 between the front end of the first portion and front end of the second portion is larger than the distance between any two points located on the third portion.

The second distance L2 between the rear end of the first portion and the rear end of the second portion is larger than the distance between any two points located on the fourth portion.

The second and third distances L2 and L3 are each larger than the distance between any two points located on the first and second portion between the front and rear ends of the first and second portion.

The absorbent layer of the pant may have no channel other than the continuous channel. Alternatively, the absorbent layer may have one or more further channels. The absorbent layer may also have no other areas, i.e. areas which are not in the shape of a channel, which are substantially free or free of absorbent material apart from the continuous channel.

Each of the front and rear belt of the disposable absorbent pant may comprise or may be formed of an inner layer, an outer layer and a plurality of elastic members disposed between the inner layer and the outer layer. The transversally lower edges of the front and the rear belt may be formed by one or both of the inner and outer layers.

The absorbent core of the pant may comprise a first substrate layer, such as a nonwoven web, provided towards the backsheet, and a second substrate layer, such as a nonwoven web, provided towards the topsheet, and absorbent material provided between first and second substrate layer, wherein the absorbent material forms the absorbent layer.

The continuous channel in the absorbent core may be substantially free, or free of absorbent material and the first and second substrate layer may be directly bonded to each other in the continuous channel.

The front end of each of the first and second portion and the third portion may overlap with the front belt. Alternatively, a part or all of third portion may overlap with the front belt while the first and second portion do not overlap with the front belt.

The central chassis may be attached to the front belt and to the rear belt. The attachment may be done by any means known in the art. For example, the central chassis may be attached to the front belt and to the rear belt by adhesive bonding, ultrasonic bonding, thermal bonding, pressure bonding, or combinations thereof. The central chassis may be attached to the front belt at least along an area at and/or adjacent to the central chassis front edge. The central chassis may be attached to the rear belt at least along an area at and/or adjacent the central chassis rear edge. The central chassis may be attached to the front and rear belt by attaching the garment-facing surface of the central chassis to the body-facing surface of the front and rear belt.

The central chassis may be provided in the disposable absorbent pant such that the chassis front edge is longitudinally spaced from the front waist edge of the pant and/or the chassis rear edge is longitudinally spaced from the rear waist edge (i.e. the chassis front edge is closer to the lateral axis that the front waist edge and/or the chassis rear edge is closer to the lateral axis than the rear waist edge). The spacing between the front waist edge and the chassis front edge may be smaller than the spacing between the rear waist edge and the chassis rear edge. E.g. the spacing between the front waist edge and the chassis front edge may be from 1.1 to 3 times, or from 1.5 to 3 times longer than the spacing between rear waist edge and the chassis rear edge.

BRIEF DESCRIPTION OF THE DRAWINGS

In the drawings, the same features are numbered consistently throughout the various views and depictions of examples.

DETAILED DESCRIPTION OF THE INVENTION

Figure 1:
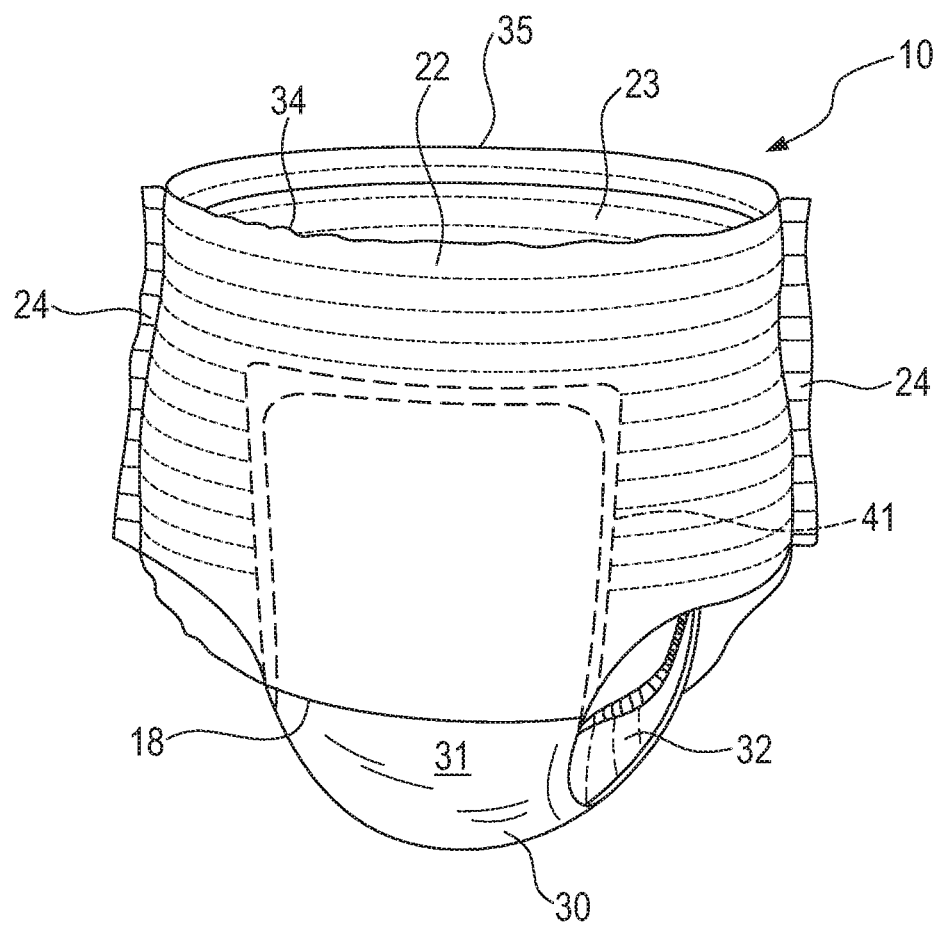
FIG. 1 is a front perspective view of an example of a disposable absorbent pant of the present invention.

As used herein, "absorbent article" refers to a device that absorbs and contains body exudates, and, more specifically, refers to a device that is placed against or in proximity to the body of the wearer to absorb and contain the various exudates discharged from the body. Absorbent articles include diapers (baby diapers and diapers for adult incontinence), pants (for babies, infants and/or for adults), absorbent inserts (which are intended to be inserted into an outer cover to form a diaper or pant), feminine care absorbent articles such as sanitary napkins or pantiliners, and the like. As used herein, the term "exudates" includes, but is not limited to, urine, blood, vaginal discharges, sweat and fecal matter. Preferred absorbent articles of the present invention are disposable absorbent articles, more preferably disposable diapers and disposable absorbent pants.

As used herein, "disposable" is used in its ordinary sense to mean an article that is disposed or discarded after a limited number of usage over varying lengths of time, for example, less than 20 usages, less than 10 usages, less than 5 usages, or less than 2 usages. If the disposable absorbent article is a diaper, a pant, sanitary napkin, sanitary pad or wet wipe for personal hygiene use, the disposable absorbent article is most often intended to be disposed after single use. The absorbent articles described herein are disposable.

As used herein, the term "comprises" is an open-ended term which means that other features, components, items or steps can be added. The term "comprises" as used herein includes the terms "essentially consisting of" and "consist of". "Consist of" denotes that only the features, components or steps following the term "consist of" are included with no further features, components, items or steps.

As used herein, "diaper" and "pant" (herein also referred to as "absorbent pant") refers to an absorbent article generally worn by babies, infants and incontinent persons about the lower torso so as to encircle the waist and legs of the wearer and that is specifically adapted to receive and contain urinary and fecal waste. In a pant, as used herein, the longitudinal edges of the first and second waist region are attached to each other to a pre-formed waist opening and leg openings. A pant is placed in position on the wearer by inserting the wearer's legs into the leg openings and sliding the pant absorbent article into position about the wearer's lower torso. A pant may be pre-formed by any suitable technique including, but not limited to, joining together portions of the absorbent article using refastenable and/or non-refastenable bonds (i.e. with permanent side seams not intended to be torn upon prior to removal of the pant from the wearer for disposal). In a diaper, the waist opening and leg openings are only formed when the diaper is applied onto a wearer by (releasable) attaching the longitudinal edges of the first and second waist region to each other on both sides by a suitable fastening system.

"Longitudinal" means a direction running substantially perpendicular from a waist edge to a longitudinally opposing waist edge of an absorbent article when the article is in a flat out, uncontracted state.

"Transverse" and "lateral" are used interchangeable herein and both terms refer to a direction running from a longitudinally extending side edge to a transversally opposing longitudinally extending side edge of an absorbent article and generally at a right angle to the longitudinal direction.

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Hot melt adhesive" as used herein refers to adhesives conforming with the description given in "Adhesion and Adhesives Technology: An Introduction" by Alphonsus V. Pocius (Hanser publishers Munich, 1997). Therein a hot melt is defined as an adhesive applied from the melt and gaining strength upon solidification.

A "nonwoven" is a manufactured sheet or web of directionally or randomly oriented fibers which are first deposited and accumulated onto a moving surface (such as a conveyor belt) and then consolidated and bonded together by friction, cohesion, adhesion or one or more patterns of bonds and bond impressions created through localized compression and/or application of pressure, heat, ultrasonic or heating energy, or a combination thereof. The term does not include fabrics which are woven, knitted, or stitch-bonded with yarns or filaments. The fibers may be of natural and/or man-made origin and may be staple and/or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwovens may be formed by many processes including but not limited to meltblowing, spunbonding, spunmelting, solvent spinning, electrospinning, carding, film fibrillation, melt-film fibrillation, air laying, dry-laying, wet laying with staple fibers, and combinations of these processes as known in the art. The basis weight of a nonwoven is usually expressed in grams per square meter ($g/m^2$).

Figure 2A:
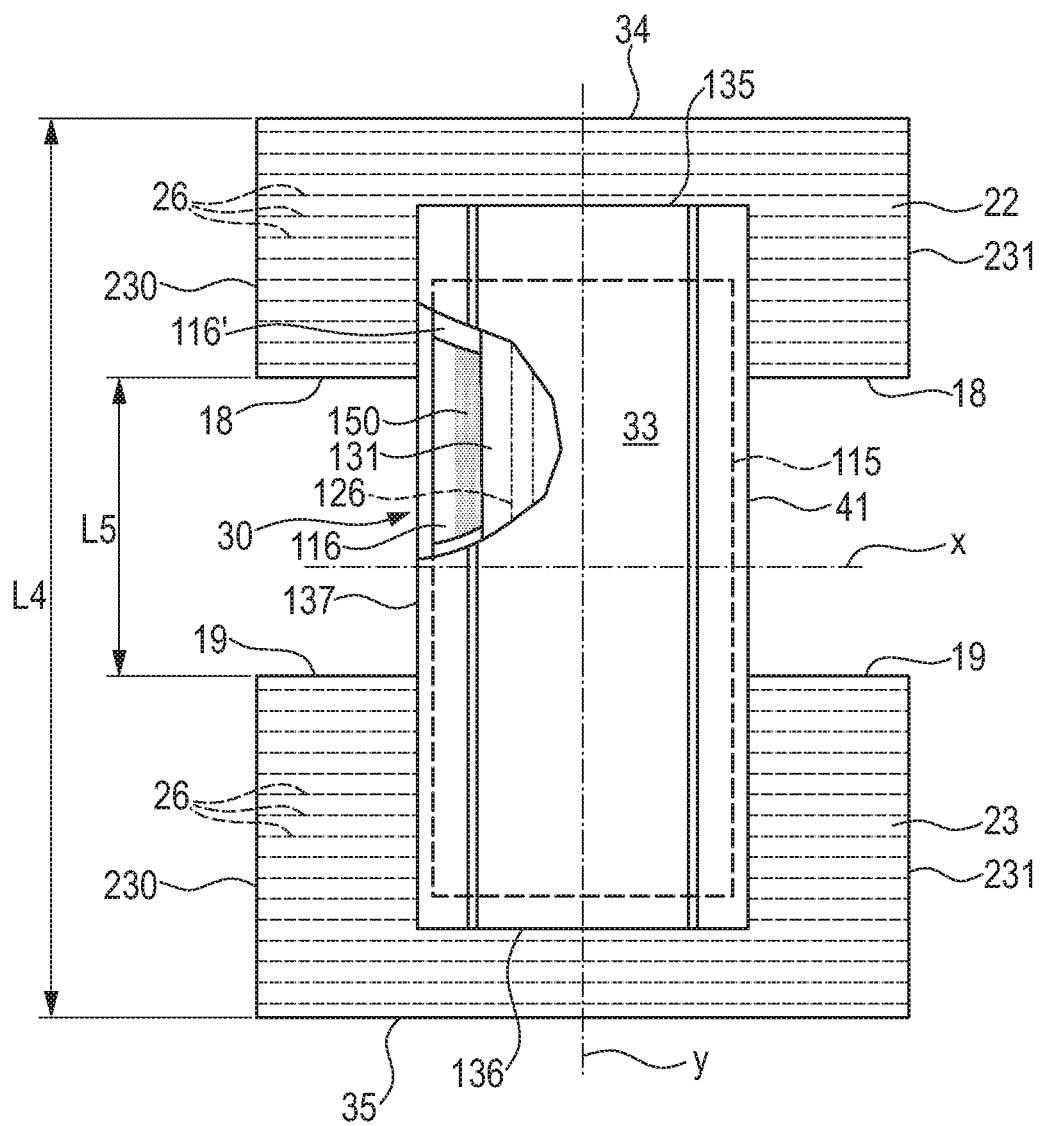
FIG. 2 A is a schematic plan view of a disposable absorbent pant of the present invention prior to joining of the front and rear belt at side seams, body-facing surfaces facing the viewer.
FIG. 2B is a schematic plan view of a disposable absorbent pant of the present invention prior to joining of the front and rear belt at side seams, body-facing surfaces facing the viewer.
FIG. 2C is a schematic plan view of a disposable absorbent pant of the present invention prior to joining of the front and rear belt at side seams, body-facing surfaces facing the viewer.
Figure 2B:
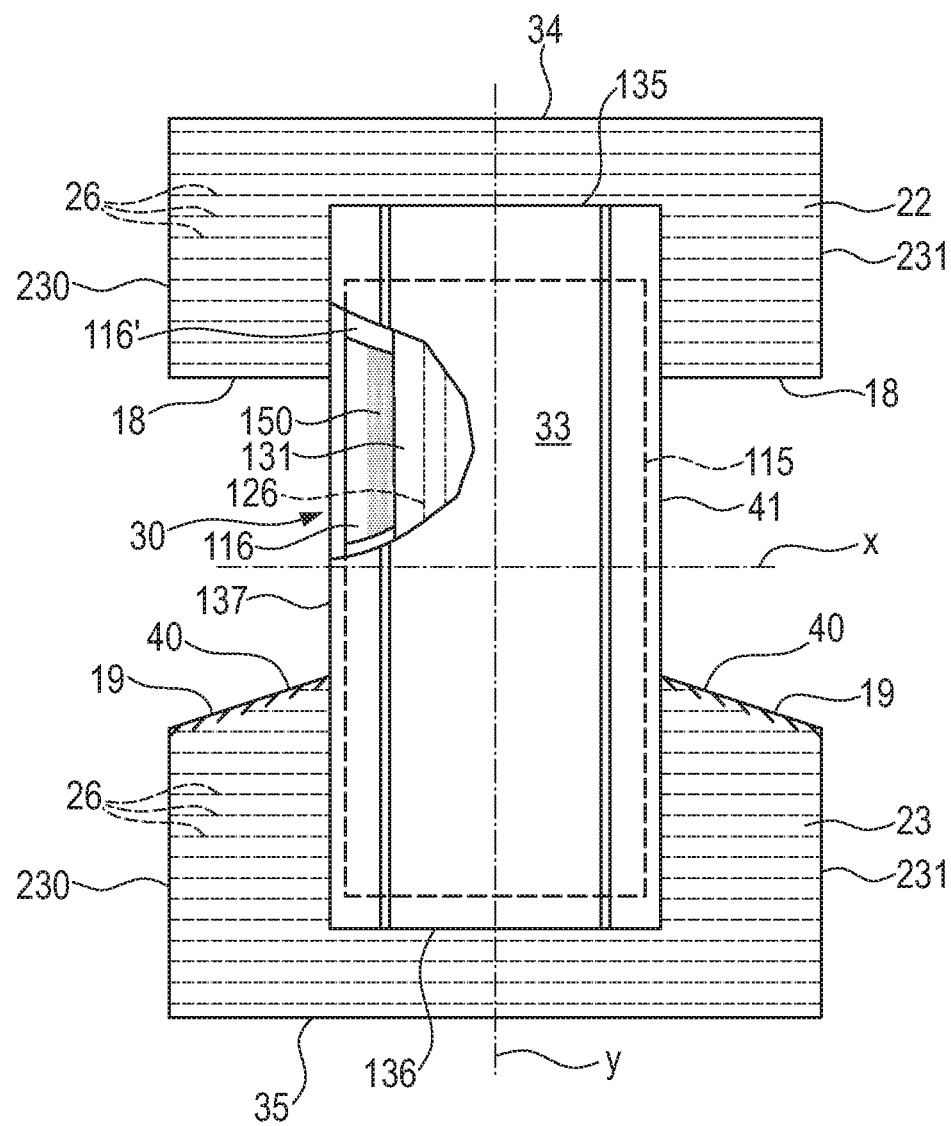
Figure 2C:
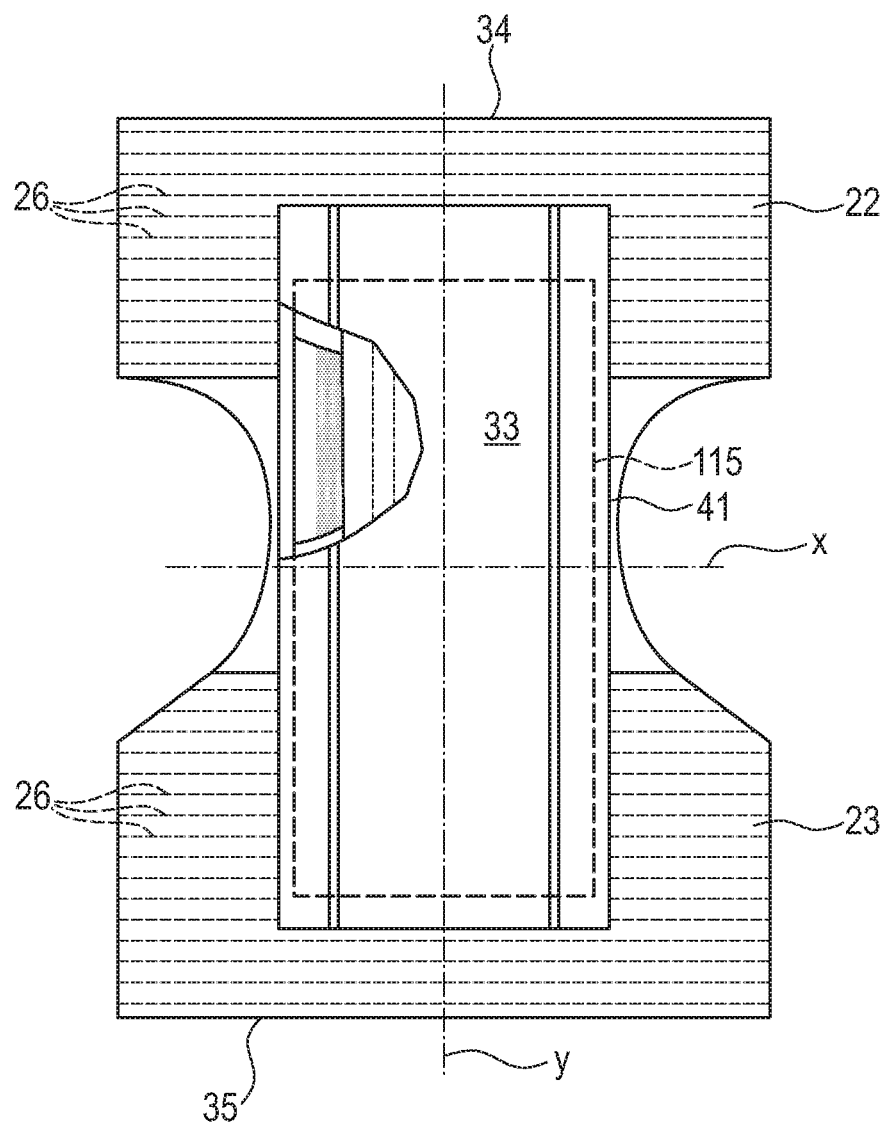

FIG. 1 depicts an example of a balloon-type absorbent pant 10. FIGS. 2A-2C depict examples of a pant in an open configuration laid out flat and stretched out laterally against elastic-induced contraction, body-facing surfaces facing the viewer, prior to final assembly in which front belt portion 22 is joined to rear belt portion 23 at seams 24. To form pant 10, the article may be folded at or about lateral axis x (located at the longitudinal midpoint of the article) with the topsheet 33 facing inward, and the longitudinal edges of the front 22 and rear 23 belt portions joined at seams 24, forming a pant structure having leg openings 15, front waist edge 34 and rear waist edge 35.

The pant structure includes an elasticized front belt 22, an elasticized rear belt 23 and a central chassis 30. Central chassis 30 may include any combination of components found in the absorbent structures of disposable diapers and absorbent pants. The central chassis 30 comprises a liquid impermeable backsheet 31, a liquid permeable topsheet 33, an absorbent core positioned between the topsheet and the backsheet. The central chassis 30 may further comprise elasticized barrier cuffs 32. Examples and descriptions of components and configurations of a central chassis 30 may be found in U.S. Pat. App. Pub. No. 2013/0211355, as well as in the other references cited herein, to the extent not inconsistent herewith, wherein the chassis described includes components and features that may be included in central chassis 30. In the example shown in FIG. 1, the front belt 22 stops at lower edge 18, thus delimiting the front waist region against the crotch region. Central chassis 30 may overly front and rear belts 22, 23 on the inside (body-facing surface) thereof. The outer perimeter 41 of the central chassis 30 may be defined by the outer perimeter of the backsheet 31.

Figure 11A:
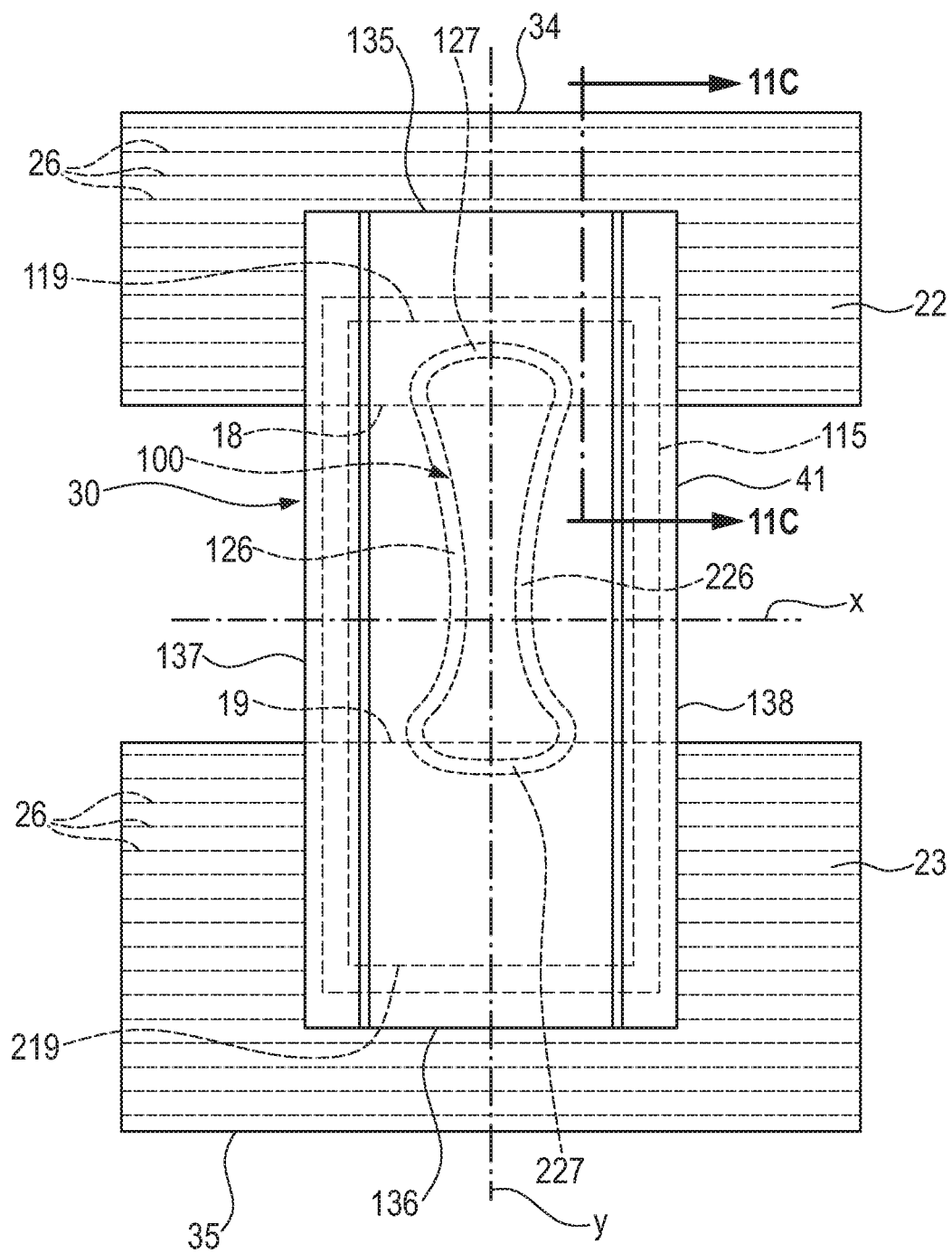
FIG. 11A is a schematic plan view of a disposable absorbent pant of the present invention, prior to joining of the front and rear belt at side seams, wearer-facing surfaces facing the viewer, shown with continuous channel in dotted lines.
Figure 11B:
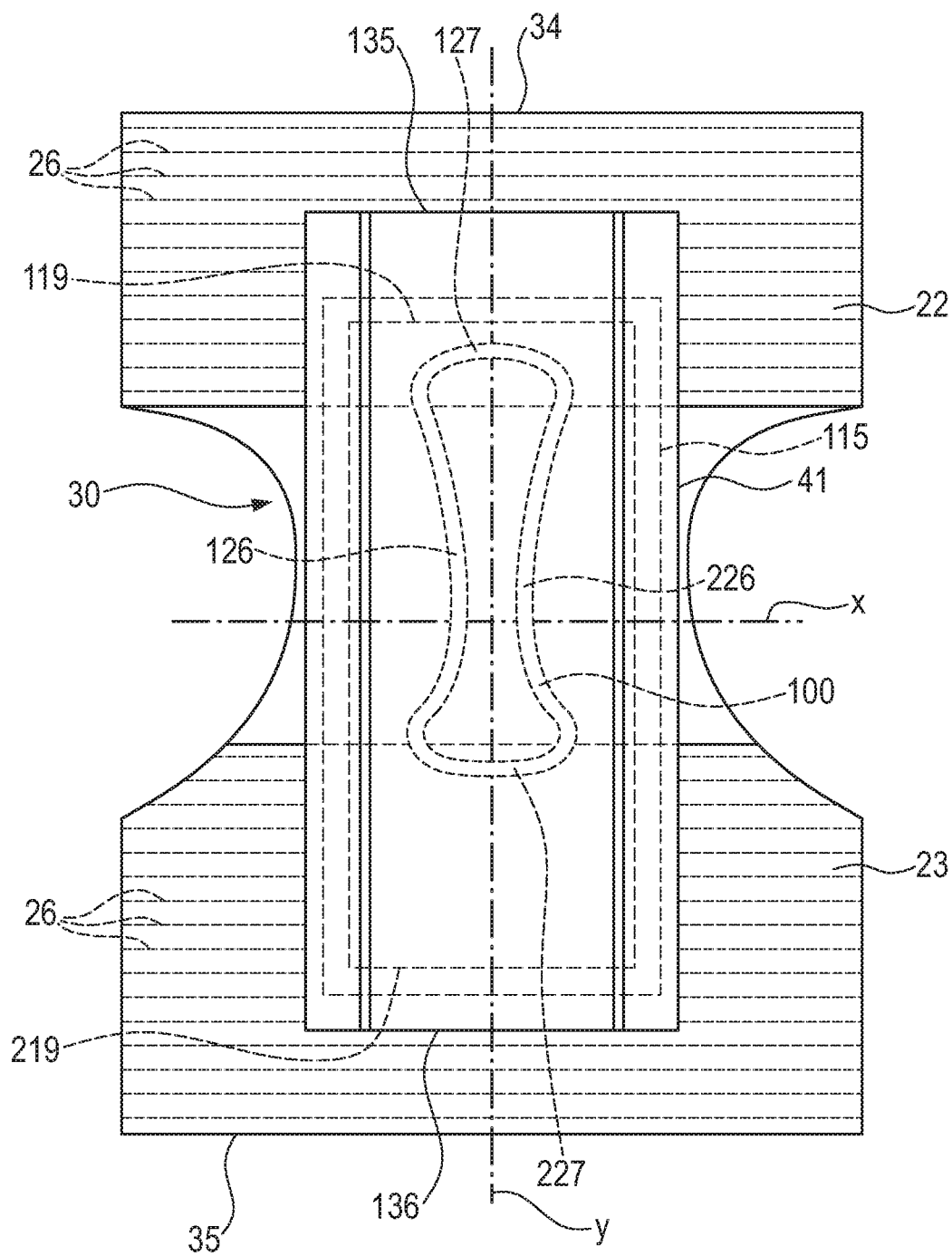
FIG. 11B is a schematic plan view of an alternate disposable absorbent pant of the present invention, prior to joining of the front and rear belt at side seams, body-facing surfaces facing the viewer, shown with continuous channel in dotted lines.

In the examples shown in FIGS. 2A and 2B, front and rear belt 22, 23 may be the outermost structures forming the front and rear waist regions of the pant. In the example illustrated in FIG. 2C (also as shown in FIG. 11B), the front and rear belt 22, 23 of the pant may extend into the crotch region such that one or more layers forming the front belt and the rear belt are continuously extending from the front waist edge 34 to the rear waist edge 35. In such pant configurations, the front belt and the rear belt are notionally divided at the transverse axis x of the pant. At least one layer may extend from the front waist edge to the rear waist edge and be formed of a continuous nonwoven web. One or more additional layers may not extend over the complete longitudinal dimension of the pant. As reflected in FIG. 2C, the one or more layers extending from the front waist edge to the rear waist edge may be cut to a profile providing suitably tailored leg opening edge profiles as desired.

Figure 3:
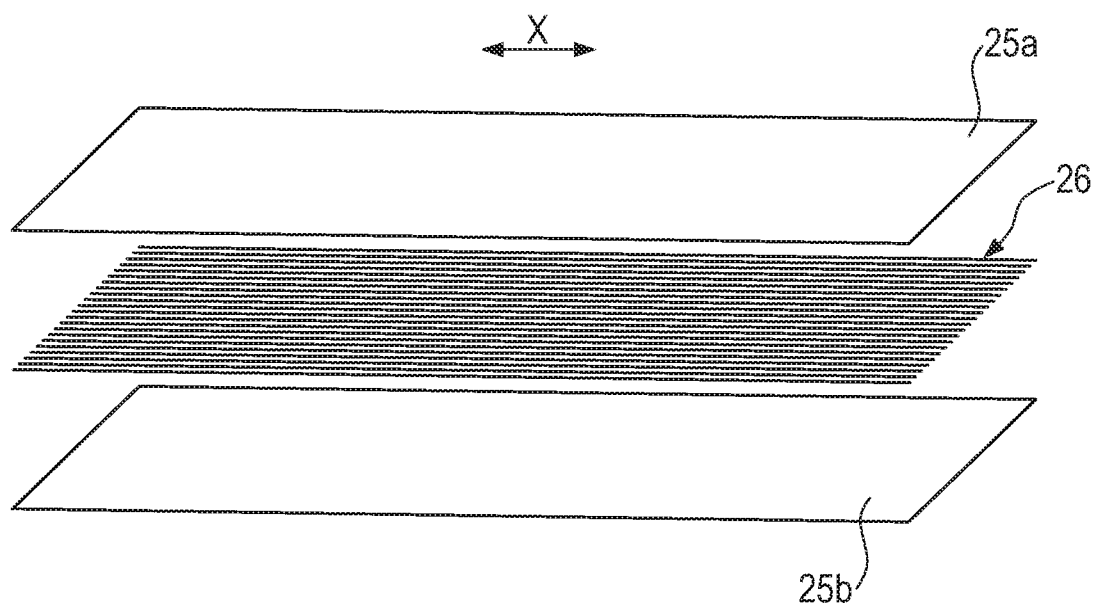
FIG. 3 is a schematic, exploded perspective view of components of a belt portion.
Figure 4:
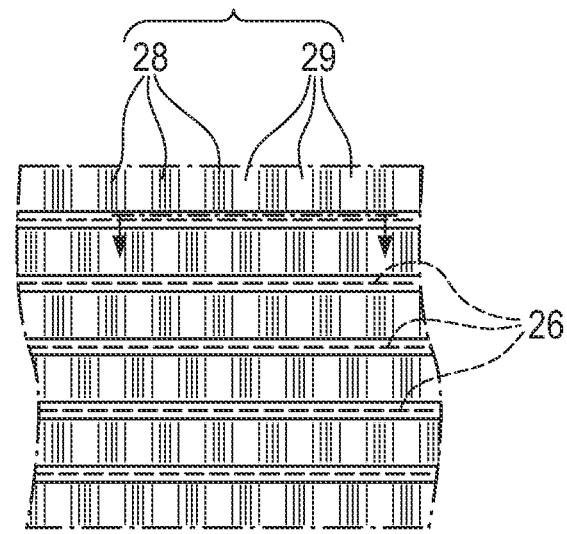
FIG. 4 is a schematic, close-up plan view of an area of a belt portion.
Figure 5:
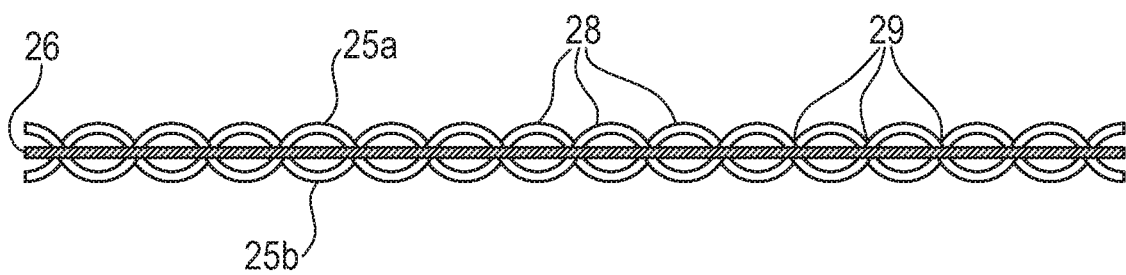
FIG. 5 is a schematic cross section of the area of the belt portion shown in FIG. 4.

Referring to FIGS. 3-5, one or both of front and rear belt 22, 23 may be formed of layers of nonwoven web 25a, 25b, which respectively form inner and outer layers. Suitable nonwoven web materials that may be useful in the present invention also include, but are not limited to spunbond, spunlaid, meltblown, spunmelt, solvent-spun, electrospun, carded, film fibrillated, melt-film fibrillated, air-laid, dry-laid, wet-laid staple fibers, and other nonwoven web materials formed in part or in whole of polymer fibers, as known in the art. The nonwoven web may be formed predominately of polymeric fibers. Suitable non-woven fiber materials may include, but are not limited to polymeric materials such as polyolefins, polyesters, polyamide, or specifically, polypropylene (PP), polyethylene (PE), poly-lactic acid (PLA), polyethylene terephthalate (PET) and/or blends thereof.

For purposes herein, use of a nonwoven web formed of crimped bicomponent or multicomponent fibers may be desired as one both layers 25a, 25b used to form the belt portions, because they can feel particularly soft to the touch (for wearer comfort on the inside and aesthetically pleasing feel on the outside) and are generally quite pliable.

Referring to FIGS. 3-5, layers of nonwoven web 25a, 25b comprised by the front and rear belt 22, 23 may sandwich one or more elastic members such as a plurality of elastic strands 26. Elastic strands may be formed of an elastomeric material, such as an elastane (for example, LYCRA HYFIT fiber, a product of Invista, Wichita, Kansas). Layers of nonwoven web 25a, 25b may be joined together about elastic strands 26 by adhesive deposited between the layers, by thermal bonds, by compression bonds, or by a combination thereof. In other examples, the one or more elastic members may be strips or a section of film formed of elastomeric material. Where the elastic member is elongate, it may be desirable that the longer dimension be laterally oriented, or even substantially aligned with the lateral direction, as strands 26 are depicted in the figures.

The elastic members can also be formed from various other materials, such as but not limited to, rubbers, styrene ethylbutylene styrene, styrene ethylene propylene styrene, styrene ethylene propylene styrene, styrene butadiene styrene, styrene isoprene styrene, polyolefin elastomers, elastomeric polyurethanes, and other elastomeric materials known in the art, and combinations thereof. The elastic members may be extruded strand elastics with any number of strands (or filaments). The elastic members can have a decitex ranging from 50 to 2000. The elastic members may be in a form of film. Examples of films have been described in prior patent applications (see, for example, U.S. Pat. App. Pub. No. 2010/0040826).

Still referring to FIGS. 3-5, during manufacture of the front and rear belt 22, 23, the elastic members such as elastic strands 26 may be pre-strained lengthwise by a desired amount as they are being incorporated into the front and rear belt 22, 23 between layers of nonwoven web 25a, 25b. Upon subsequent relaxation of the belt, the elastic members, such as elastic strands 26, will contract laterally toward their unstrained lengths. This causes the layers of nonwoven web 25a, 25b to gather and form ruffles or rugosities 27 having ridges 28 and valleys 29 generally transverse to the lengths of the elastic strands 26, and extending in the z-direction (i.e. the direction perpendicular to both the lateral and the longitudinal axis).

In another example, to adhere the components of the belt laminate, the elastic strands 26 themselves may be individually coated with adhesive ("strand coated") prior to incorporation between layers of nonwoven web 25a, 25b to form the front and rear belt 22, 23. Various coating methods and techniques, including strand coating methods and techniques, are shown for example in U.S. Pat. Nos. 5,340,648; 5,501,756; 5,507,909; 6,077,375; 6,200,635; 6,235,137; 6,361,634; 6,561,430; 6,520,237; 6,582,518; 6,610,161; 6,613,146, 6,652,693, 6,719,846 and 6,737,102. The adhesive used may be a hot-melt type adhesive having elasticity and flexibility making it suitable for attaching pre-strained elastic materials to substrates, such as OMNIMELT BLOCKS 22 H2401F, or ZEROCREEP brands such as A VANCE, available from Bostik, Inc., Wauwatosa, Wisconsin.

Figure 6A:
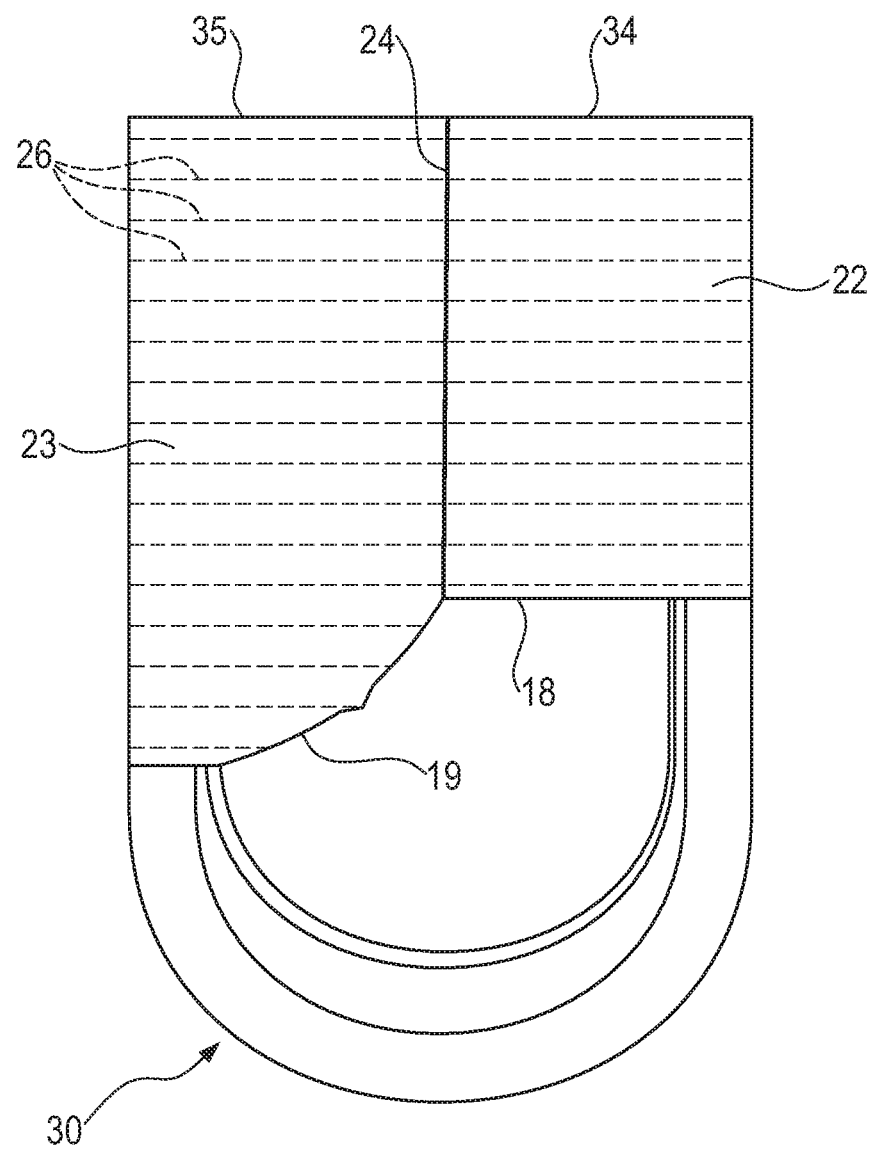
FIG. 6A is a schematic side view of a disposable absorbent pant of the present invention.

Referring e.g. to FIG. 2A, the rear belt 23 may have a greater longitudinal dimension (i.e., greater length) than the front belt 22. This may help provide greater coverage of the wearer's buttocks area in the rear while providing greater comfort in front, via better conformity with wearer anatomy and natural body movement. In the example of FIG. 2A, when the front and rear belt 22, 23 are joined at side seams 24 along their respective first and second longitudinally extending side edges at side seams with their respective waist edges 34, 35 substantially aligned, however, the second lower edge 19 of the rear belt 23 will lie below the first lower edge 18 of the front belt 22 to form a stepped leg edge profile at the seams 24. If deemed undesirable, this effect may be mitigated by selecting, disposing and/or varying pre-strain levels among the elastic members as suggested and described in, for example, U.S. Pat. App. Ser. No. 62/042,387, to laterally draw the lower rear corners of the rear belt 23 (i.e. the corner where the first and second longitudinally extending side edges of the rear belt meets the second lower edge 19 of the rear belt 23) inward toward the longitudinal axis y. A potential desirable result of such practice is schematically suggested in FIG. 6A.

Figure 6B:
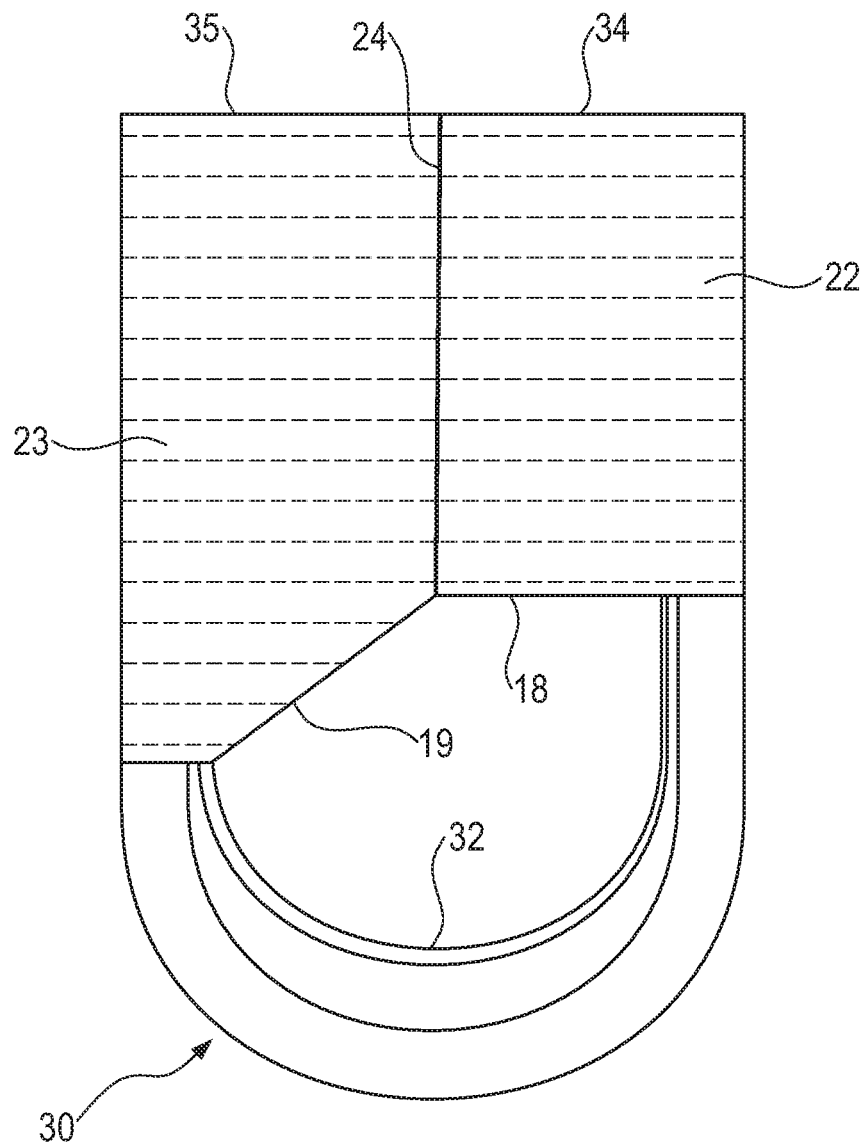
FIG. 6B is a schematic side view of a disposable absorbent pant of the present invention.

Alternatively, the lower portions of the first and second longitudinally extending side edges below the side seams 24 of the rear belt 23 and/or the second lower edges 19 laterally outside of the area where the rear belt 23 overlays the central chassis 30 may be trimmed off as suggested in FIGS. 2B and 6B. Such trimming may be done along straight lines as suggested in FIGS. 2B and 6B, or may follow a trim path that are curved (as exemplified in FIG. 6A) and either concave or convex with respect to the remaining area of the rear belt 23, as may be desired to impart a particular curved rear leg edge profile.

In conjunction with such trimming and the configuration of elastic strands described above, it may be desired to impart bonding 40 between layers 25 a, 25b along the trimmed second lower edges 19 and/or the lower portions of the first and second longitudinally extending side edges below the side seams 24 of rear belt 23. Such bonding may serve to prevent any separation of the layers along the edges that may contribute to creating a ragged appearance, and may also help the rear belt 23 more effectively draw inward laterally toward the central chassis 30, under the contractive force of the elastic strands below the side seams 24. Bonding 40 may be effected by mechanical/compression bonds as described in, for example, U.S. Pat. Nos. 4,854,984 and 4,919,738, by thermal bonds or welds, or by deposits of adhesive between nonwoven layers 25 a, 25b. As suggested in FIG. 2B, such bonding may form a pattern along the edges. Such bonding may be supplemental to any bonding between layers 25a, 25b generally holding rear belt 23 together as a laminate structure.

Side seams 24 may be permanent or refastenable. Permanent seams may be formed between the front belt portion and the rear belt portion by any bonding mechanism wherein the first and second longitudinally side edges 230, 231 of front and rear belt 22, 23 may not be forcibly separated without substantial damage to one or both of the front and rear belt 22, 23. Bonding forming permanent side seams 24 may include pressure bonding, thermal bonding/welds, ultrasonic bonding, adhesive bonding or combinations thereof.

Refastenable side seams 24 may be formed between the front belt 22 and the rear belt 23 by any mechanism configured to permit substantially non-destructive forcible separation of the front and rear belt 22, 23, and subsequent substantial reattachment or refastening at the same locations. One example of such mechanism is a hook-and-loop fastening system, for example, a VELCRO fastening system. A suitably sized and shaped hook component may be bonded to one of the front or rear belt along the first and second longitudinal side edges 230, 231 thereof, and suitably sized and shaped loops component may be bonded to the other of the front or rear belt along the first and second longitudinal edges 230, 231 thereof, in positions in which they may be brought together and engaged to form seams 24. Examples are depicted in U.S. Pat. App. Ser. Nos. 61/787,416; 61/787,332; 61/666,065.

Absorbent Core

The absorbent core 115 includes an absorbent layer 117 which may include superabsorbent polymer particles, and optionally cellulose fibers. The absorbent layer 117 may be supported by, and immobilized on, one or more substrate layers 116, 116', such as a first substrate layer 116 provided towards the backsheet 31 of the central chassis 30 and a second substrate layer 116' provided towards the topsheet 33 of the central chassis, with the absorbent layer being sandwiched in between the first and second substrate layer 116, 116'. Examples of absorbent structures 115 are illustrated in FIGS. 7, 9, 10A and 10B.

The first and/or second substrate layer 116, 116' of the absorbent core may be any material capable of supporting the superabsorbent polymer particles. It may be a web or sheet material, such as foam, film, woven or, preferably, a nonwoven web. The first and second substrate layer 116, 116' may be distinct separate sheets of material (such as two nonwoven webs) or may be formed of a continuous sheet (such as a continuous nonwoven web) which is wrapped around the absorbent layer.

The first and second substrate layers 116, 116' and the absorbent layer 117 may be coextensive or the first and/or second substrate layer 116, 116' may be slightly longer and wider than the absorbent layer 117 (as suggested in FIGS. 7, 9, 10A and 10B).

The absorbent layer 117 may include superabsorbent polymer particles 150, and optionally cellulose fibers. The absorbent layer may include absorbent polymer in other forms such as superabsorbent polymer fibers. Superabsorbent polymer particles. The absorbent layer may include superabsorbent polymer particles combined with cellulose. "Cellulose" as used herein refers to comminuted wood pulp in the form of fibers, sometimes also referred in the art as "air-felt".

The absorbent layer may comprise more than 70%, or more than 80%, or more than 90%, or more than 95% or even 100% of superabsorbent polymer particles by weight of the absorbent layer. The absorbent layer may include superabsorbent polymer particles and less than 5% by weight of cellulose, or less than 2% by weight of cellulose, or even no cellulose. When the absorbent layer is cellulose free, the only absorbent material in the absorbent layer may be superabsorbent polymer (particles or fibers). The resulting absorbent cores have a reduced thickness in the dry state compared to conventional absorbent cores including cellulosic fibers. The reduced thickness helps to improve the fit and comfort of the absorbent article for the wearer.

Alternatively, the absorbent layer may comprise a mixture of superabsorbent polymer particles and cellulose fibers. The absorbent layer may comprise more than 20%, or more than 30%, or more than 40%, by weight of the absorbent layer, of cellulose fibers. The superabsorbent polymer particles and the cellulose fibers may be homogeneously mixed with each other such that the ratio of cellulose fibers to superabsorbent polymer particles is substantially the same throughout the absorbent layer. Alternatively, the superabsorbent polymer particles and the cellulose fibers may be non-homogeneously mixed such that the ratio of cellulose fibers to superabsorbent polymer particles is higher towards the front and rear edges of the absorbent layer compared to a central area of the absorbent layer. The area towards the front edge of the absorbent layer, the area towards the rear edge of the absorbent layer, and the central area may each extend along ⅓ of longitudinal dimension of the absorbent layer along the longitudinal axis.

Continuous Channel

The absorbent layer 117 comprises a continuous channel 100. A "continuous channel", as used herein, refers to a channel with no defined beginning and end as it is a channel which is closed in itself and self-contained, i.e. it is ring-shaped but not circular. The continuous channel 100 has a first, second, third and fourth portion 126, 226, 127 and 227.

"Channels" as used herein refers to troughs or other identifiable elongate passageways through the deposit of absorbent material in the absorbent layer (see e.g. FIGS. 2A, 2B and 7-9).

The continuous channel (and any further channel, if present) may extend partially or, preferably, entirely through the thickness of the absorbent layer 117. If the continuous channel 100 (and any further channel, if present) extends entirely through the thickness of the absorbent layer 117, substantially no absorbent material is present in the continuous channel 100. "Substantially no absorbent material" means that either no absorbent material at all or insignificant amounts of absorbent material are present. For example, trace amounts of superabsorbent polymer particles and/or cellulose fibers may be present in the continuous channel which may be due to slight deviations in the manufacturing of the absorbent core, which typically runs at high speed.

The first and second portion 126, 226 formed in the absorbent layer 117 are each longitudinally-oriented elongate portions. The third and fourth portion 127 and 227 are each laterally-oriented elongate portions.

The first portion is provided between the longitudinal axis y and the first side edge 118 of the absorbent layer 117. The second portion is provided between the longitudinal axis y and the second side edge 218 of the absorbent layer 117.

The first and second portion 126, 226 each have a front end 215 towards the absorbent layer's front edge 119, a rear end 216 towards the absorbent layer's rear edge 219 and a center 214 which is equally spaced from the respective's front and rear end 215, 216 across the longitudinal axis y. Each of the first and second portion 126, 226 is curved such that the first and second portion are closer to the longitudinal axis y at a location (the "necking point" 220) between the front end and the rear end of the respective first and second portion, than the portion's front and rear ends 215, 216.

The necking point may be located between the center and the rear end of each of the respective first and second portion. The necking point 220 of the first portion 126 may be spaced from 5% to 30%, or from 5% to 25%, or from 10% to 25% away from the center 214 of the first portion towards the rear end 216, based on the total length of the first portion 126, as measured along a straight line from the front end 215 to the rear end 216 of the first portion 126.

Likewise, the necking point 220 of the second portion 226 may be spaced from 5% to 30%, or from 5% to 25%, or from 10% to 25% away from the center 214 of the second portion 226 towards the rear end 216, based on the total length of the second portion 226, as measured along a straight line from the front end 215 to the rear end 216 of the second portion 226.

The third portion 127 connects the front end 215 of the first portion 126 with the front end 215 of the second portion 226 and extends from the front end 215 of the first portion 126 to the front end 215 of the second portion 226.

The fourth portion 227 connects the rear end 216 of the first portion with the rear end 215 of the second portion and extends from the rear end 216 of the first portion 126 to the rear end 216 of the second portion 226.

The first and second portion 126 and 226 may each not be closer to the longitudinal axis y at any other location than at their necking point 220. If the necking point of the first portion 126 is located at a straight section (i.e. a non-curved section) which is parallel to the longitudinal axis y, then the necking point is the midpoint of this straight section. For example, if the first portion comprises a straight section parallel to the longitudinal axis y which is 3 cm long and closer to the longitudinal axis y than any other part of the first portion, than the necking point is the midpoint of the 3 cm along the longitudinal dimension of the straight section. Similarly, if the necking point of the second portion 226 is located at a straight section (i.e. a non-curved section) which is parallel to the longitudinal axis y, then the necking point is the midpoint of this straight section. For example, if the second portion comprises a straight section parallel to the longitudinal axis y which is 3 cm long and closer to the longitudinal axis y than any other part of the second portion, than the necking point is the midpoint of the 3 cm along the longitudinal dimension of the straight section.

Alternatively, the necking point of the first portion may be closer to the longitudinal axis y than any other part of the first portion first. The necking point of the second portion may be closer to the longitudinal axis y than any other part of the second portion.

Figure 7:
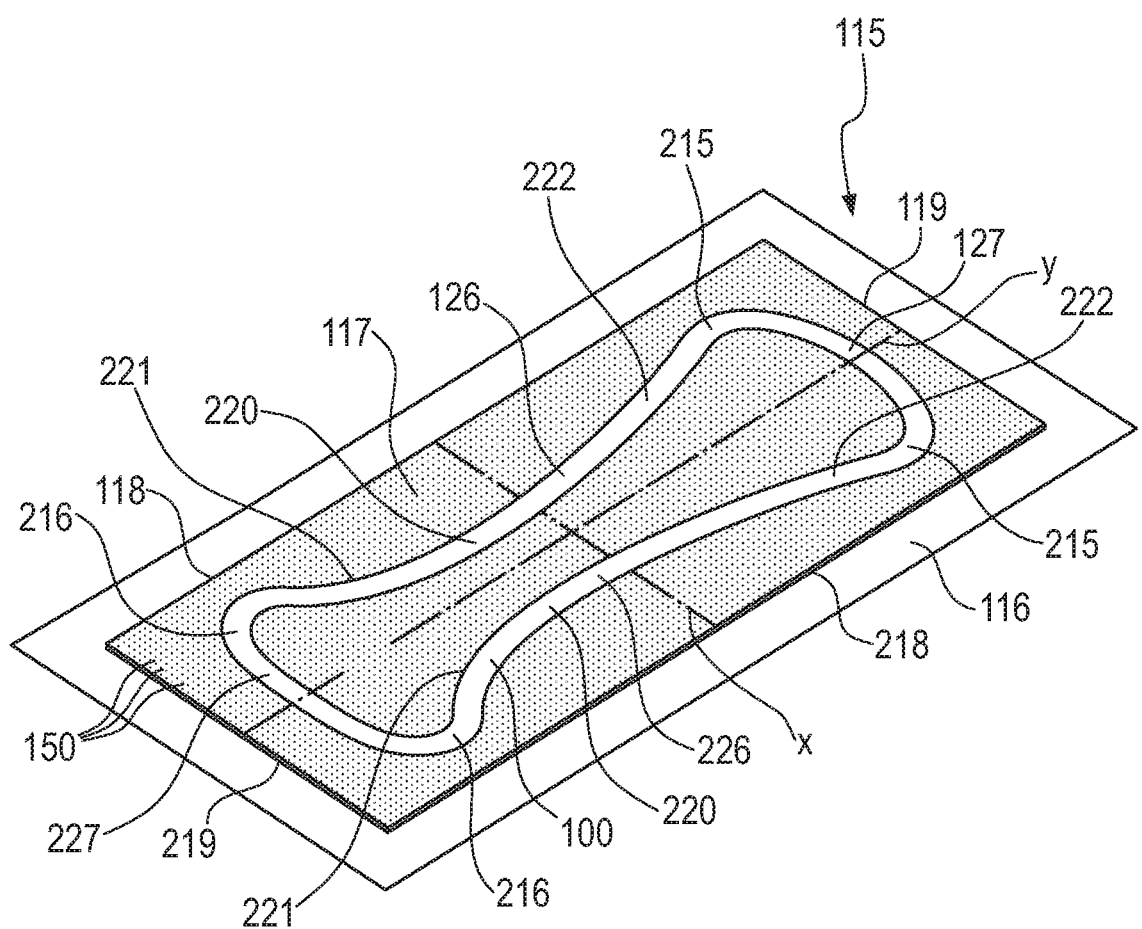
FIG. 7 is a schematic perspective view of an absorbent layer with a first substrate layer and including a continuous channel for use in a disposable absorbent pant of the present invention.
Figure 8:
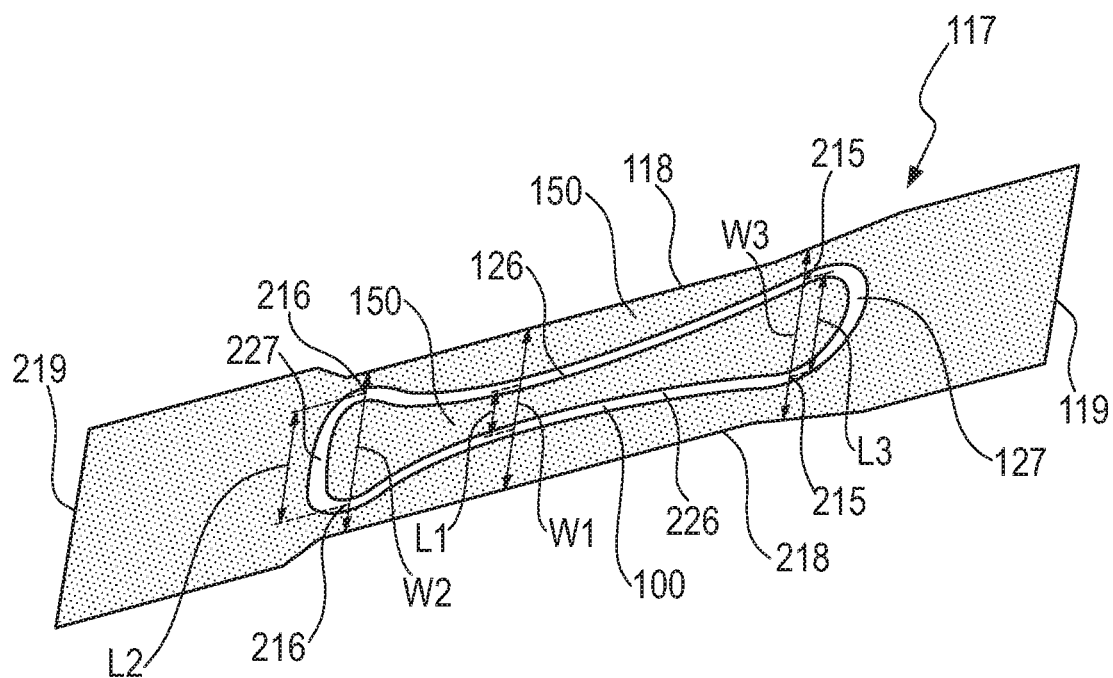
FIG. 8 is a schematic perspective view of an absorbent layer including a continuous channel for use in a disposable absorbent pant of the present invention.
Figure 9A:
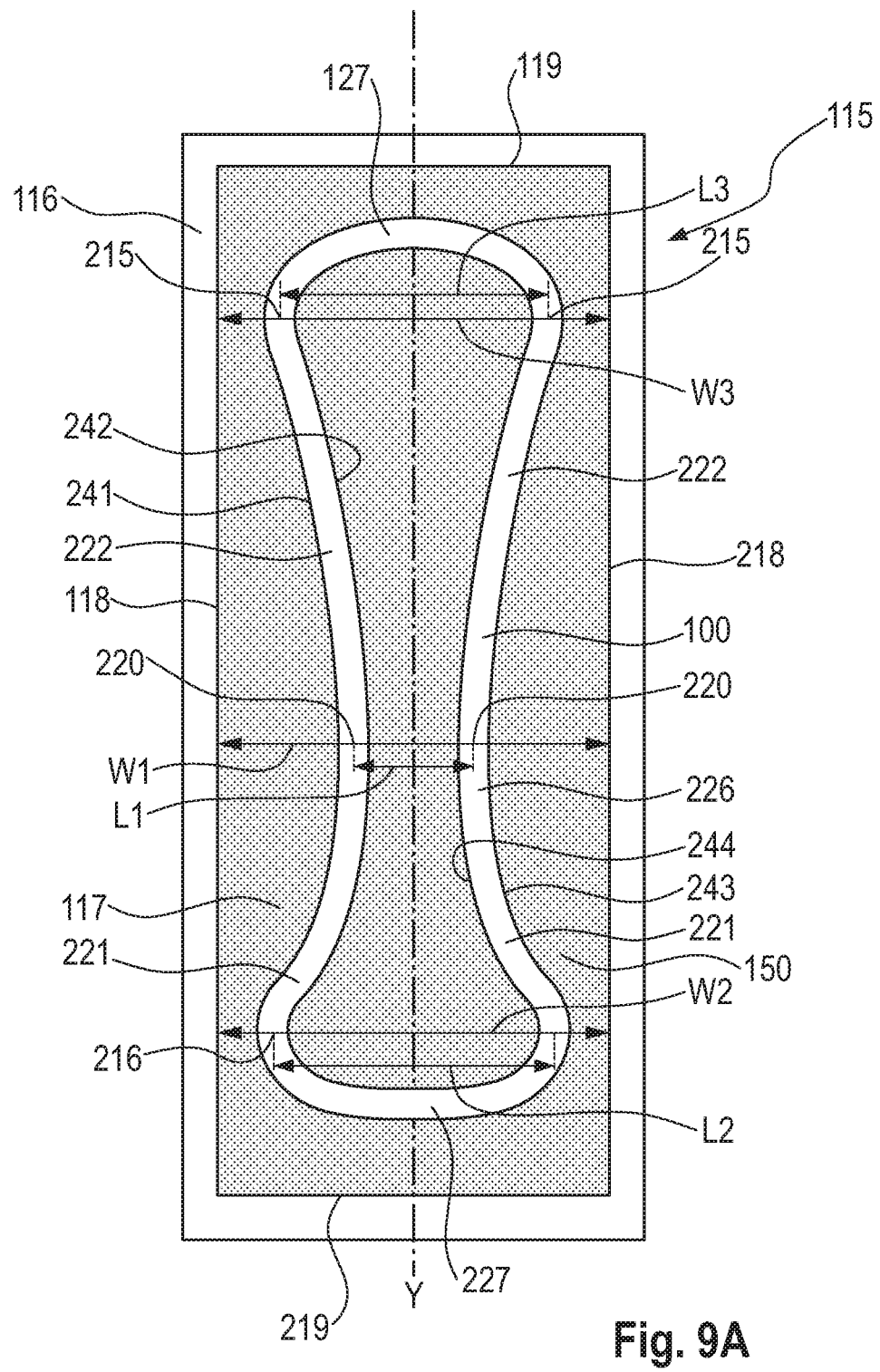
FIG. 9A is a schematic top/plan view of an absorbent layer with a first substrate layer and including a continuous channel for use in a disposable absorbent pant of the present invention.
Figure 9B:
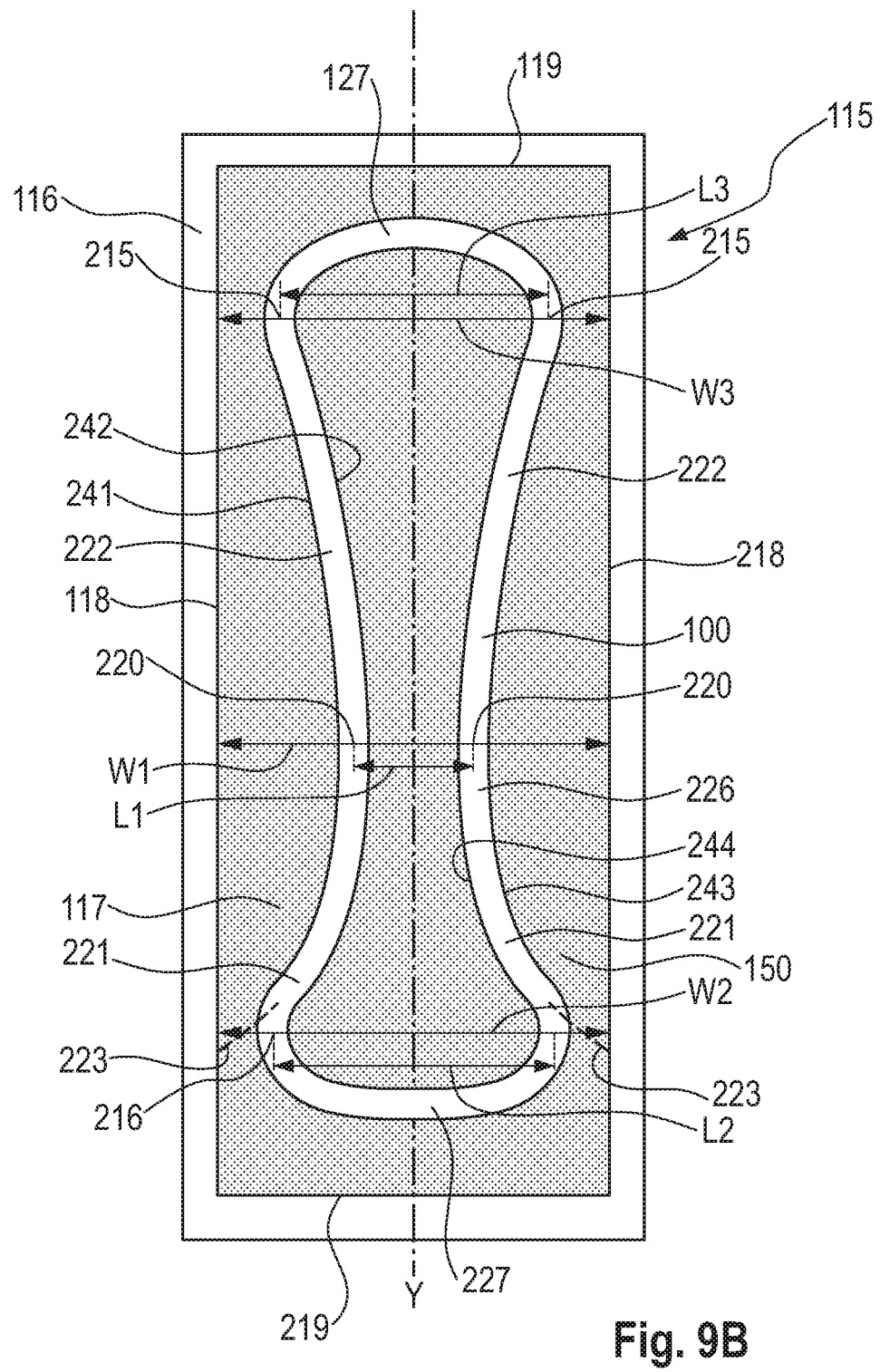
FIG. 9B is similar to FIG. 9A and additionally shows (in dotted lines) fold lines continuing outwardly from the first and second portion of the continuous channel towards the rear edge of the absorbent layer.

The first portion 126 may follow a first curved path 221 with only one curve between the necking point 220 and the rear end 216 of the first portion 126. The first portion 126 may follow a second curved path 222 with only one curve between the necking point 220 and the front end 215 of the first portion 126. The first curved path 221 of the first portion 126 may have a steeper curvature compared to the second curved path 222 of the first portion 126. Examples of such portion configuration are shown in FIGS. 7, 8 and 9.

Likewise, the second portion 226 may follow a first curved path 221 with only one curve between the necking point 220 and the rear end 216 of the second portion 226. The second portion 226 may follow a second curved path 222 with only one curve between the necking point 220 and the front end 215 of the second portion 226. The first curved path 221 of the second portion 226 may have a steeper curvature compared to the second curved path 222 of the second portion 226. Examples of such portion configuration is shown in FIGS. 7, 8 and 9.

The first, second, third and fourth portion 126, 226, 127, 227 of the continuous may have a perimeter which delimits each portion, and in conjunction, the continuous channel as a whole, against the absorbent layer surrounding it.

Each of the first and second portion 126, 226 may have a first and a second longitudinal edge on each side along its length. The first longitudinal edge 241 of the first portion 126 is formed towards the first longitudinal side edge 118 of the absorbent layer 117 and the second longitudinal edge 242 of the first portion 126 is formed towards the longitudinal axis y. The first longitudinal edge 243 of the second portion 226 is formed towards the second longitudinal side edge 218 of the absorbent layer 117 and the second longitudinal edge 244 of the second portion 226 is formed towards the longitudinal axis y. The middle between the first and second longitudinal edges of the first portion is halfway between the first and second longitudinal edge as measured at a given location of the first portion by taking the shortest distance between the first and second longitudinal edges at this location (e.g. at the necking point of the first portion). Likewise, the middle between the first and second longitudinal edges of the second portion is halfway between the first and second longitudinal edge as measured at a given location of the second portion by taking the shortest distance between the first and second longitudinal edges at this location (e.g. at the necking point of the second portion).

Each of the third and fourth portion 127, 227 may have a first and a second lateral edge on each side along its length. The first lateral edge of the third portion 127 is formed towards the front edge 119 of the absorbent layer 117 and the second lateral edge of the third portion 127 is formed towards the lateral axis x. The first lateral edge of the fourth portion 227 is formed towards the rear edge 219 of the absorbent layer 117 and the second lateral edge of the fourth portion 227 is formed towards the lateral axis x. The middle between the first and second lateral edges of the third portion is halfway between the first and second lateral edge as measured at a given location of the third portion by taking the shortest distance between the first and second lateral edges at this location. Likewise, the middle between the first and second lateral edges of the fourth portion 227 is halfway between the first and second lateral edges as measured at a given location of the fourth portion by taking the shortest distance between the first and second lateral edges at this location.

The third and fourth portion 127, 227 each have a center. The center of the third portion 127 is halfway between the front end 215 of the first portion 126 and the front end 215 of the second portion 226. The center of the fourth portion 227 is halfway between the rear end 216 of the first portion 126 and the rear end 216 of the second portion 226.

The first longitudinal edge 241, 243 of each of the first and second portion 126, 226, together with the first lateral edge of each of the third and fourth portion 127, 227 form the outer boundary of the continuous channel 100. The second longitudinal edge 242, 244 of each of the first and second portion 126, 226 together with the second lateral edge of each of the third and fourth portion 127, 227 form the inner boundary of the continuous channel 100.

The first and second portion 126, 226 are spaced apart from each other at their necking point 220 by a first distance L1. The distance L1 is measured between the middle of the first portion 126 at the first portion's necking point 220 and the middle of the second portion 226 at the second portion's necking point 220.

The absorbent layer 117 has a first transverse width W1 extending from the first longitudinally extending side edge 118 to the second longitudinally extending side edge 218 of the absorbent layer 117 across the necking point of the first and second portion.

The distance L1 is from 20 mm to 50 mm, or from 25 mm to 45 mm, or from 30 mm to 45 mm, or from 35 mm to 45 mm.

The first transverse width W1 may be from 50 mm to 150 mm, or from 50 mm to 130 mm, or from 50 mm to 115 mm, or from 60 mm to 115 mm, or from 80 to 115 mm.

The first and second portion 126, 226 are spaced apart from each other at their rear ends 216 by a second distance L2. The second distance L2 is measured between the middle of the first portion 126 at the first portion's rear end and the middle of the second portion 226 at the second portion's rear end. The second distance L2 may be from 48 mm to 70 mm, or from 50 mm to 65 mm, or from 50 mm to 60 mm. The second distance L2 is larger than first distance L1.

The absorbent layer 117 has a second transverse width W2 extending from the first longitudinally extending side edge 118 to the second longitudinally extending side edge 218 of the absorbent layer 117 across the rear ends 216 of the first and second portion 126, 226. The second transverse width W2 may be from 50 mm to 150 mm, or from 50 mm to 130 mm, or from 50 mm to 115 mm, or from 60 mm to 115 mm, or from 80 to 115 mm.

The second transverse with W2 may the equal to the first transverse width W1. Alternatively, the second transverse width W2 may be larger than the first transverse width W1. The second transverse width W2 may be at least 10% larger, or at least 15% larger, or at least 20% larger, or at least 25% larger than the first transverse width W1. The second transverse width W2 may not be more than 60%, or not more than 50%, or not more than 40%, or not more than 30% larger than the first transverse width W1.

The ratio of the second transverse width W2 to the second distance L2 is from 1.5 to 2.8.

The ratio of the first transverse width W1 to the first distance L1 is higher than the ratio of the second transverse width W2 to the second distance L2.

The ratio of L2 to L1 is from 1.2 to 2.5, or from 1.4 to 2.2, or from 1.5 to 2.0.

The first and second portion may both extend across the transverse axis x of the absorbent pant. They may be provided such that the center of each of the first and second portion is provided offset from the lateral axis x towards the front waist edge. For example, the center of each of the first and second portion may be provided from 30% to 48%, or from 35% to 44% from the front waist edge of the pant based on the overall length L4 of the pant.

The first and second portion may substantially be mirror images of each other and may have substantially no offset to each other along the longitudinal axis. "Substantially" mirror images and "substantially" no offset means to include insignificant deviations which may, for example be due to variations of a high-speed manufacturing process variations. "Substantially" no offset includes an offset of up to 10%, or up to 5% based on the length of the portion as measured along the longitudinal axis along a straight line from the front end to the rear end of the portion. The first and second portion may be mirror images of each other and may have no offset to each other along the longitudinal axis.

The first and second portion may have substantially the same length as measured along the longitudinal axis along a straight line from the front end to the rear end of the portion. "Substantially" the same length includes deviations in length of up to 10%, or up to 5% based on the length of the longer portion. The first and second portion may have the same length.

Figure 12:
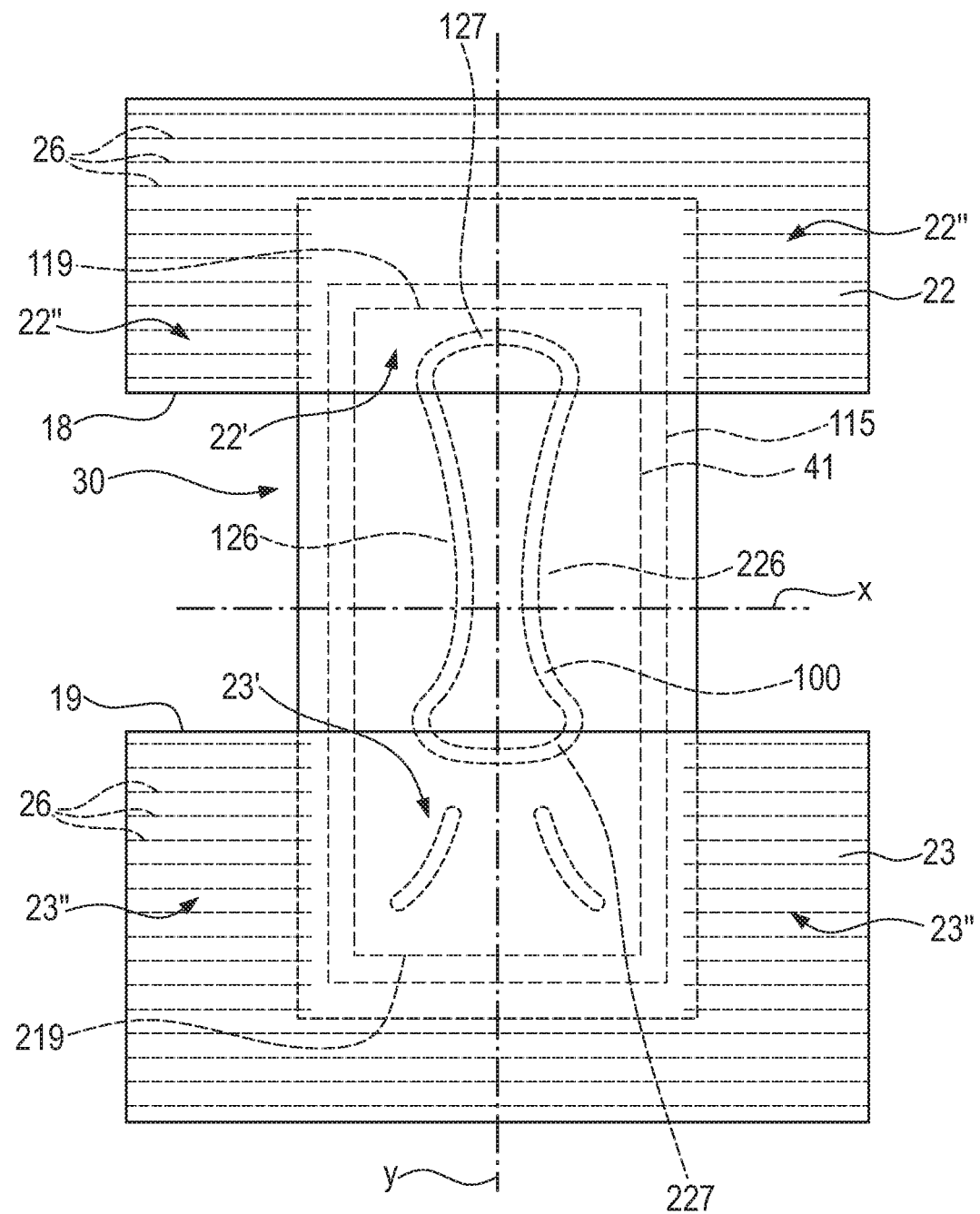
FIG. 12 is a schematic plan view of a disposable absorbent pant of the present invention prior to joining of the front and rear belt at side seams, garment-facing surfaces facing the viewer, shown with non-elasticized zones in front and rear belt.

The absorbent layer may have no other channels than the continuous channel. Alternatively, the absorbent layer may comprise further channels, which are not continuous. For example, the absorbent layer may have one or more elongate curved channels, each of which being shorter in in their longest dimension (as measured along a straight line from their one end to their other end) than the first and second portion of the continuous channel. The one or more channels provided in addition to the continuous channel may be straight or curved, or one or more additional channels may be straight while other additional channels are curved. FIG. 12 illustrates two additional curved channels provided towards the rear edge of the absorbent layer, one channel being provided between the first longitudinally extending side edge of the absorbent layer and the longitudinal axis y, the other channel being provided between the second longitudinally extending side edge of the absorbent layer and the longitudinal axis y. As shown in FIG. 12, these two additional channels may be mirror-images of each other, which are equally spaced away from the longitudinal axis y towards the first and second longitudinally extending side edge, respectively, of the absorbent layer.

With the first distance L1 being from 30 mm to 50 mm, the ratio of the second transverse width W2 to the second distance L2 being from 1.5 to 2.8, the ratio of the second length L2 to first length L1 being from 1.2 to 2.5 and the ratio of W1 to L1 being higher than the ratio of W2 to L2, these dimensions and ratios in combination define an absorbent layer wherein the continuous channel, and especially the first and second portions of the continuous channel are configured such that the central chassis of absorbent pant has an improved fit. As already explained above, when the pant is being pulled up between the legs of the wearer upon application onto a wearer, the central chassis tends to fold in order to accommodate between the relatively narrow space between the legs. Having the absorbent layer and continuous channel with the first and second portion being configured in the claimed manner, helps to prevent that the central chassis folds too narrowly, both in the crotch and towards the rear waist region.

The first and second portion are spaced apart from each other across their necking point relatively widely compared to known longitudinally elongate channel configurations. If the first and second portions are arranged in closer proximity to each other, the central chassis will tend to fold into a relatively narrow U-shape between the legs of the wearer, which may lead to a wider gap between the absorbent core and the body of the wearer in the crotch. This increases the risk of leakage due to reduced contact of the central chassis with the body of the wearer and due to the narrow fold which leads to bunching of the absorbent core between the wearer's legs.

As the necking point is not necessarily provided at the center of the first and second portion but, preferably, between the center and the rear end of the first and second portion, the fit is further improved. With the necking point being offset from the center towards the rear end, the first curved path between the necking point and the rear end of each of the first and second portion can follow a stepper curvature compared to the second curved path between the necking point and the front end of the first and second portion.

As said, the absorbent layer—and thus the central chassis as a whole—tends to fold inwardly along the first and second portions. For pants, pulled awards on the wearer into their final wearing position, this folding typically extends beyond the ends of the first and second portion into the absorbent layer towards the front and rear edges of the absorbent layer. Having a steeper curvature along the first curved path towards the rear end of the first and second portion results in the fold lines continuing into the absorbent layer beyond the first and second portion's rear end being directed towards the longitudinally extending side edges of the absorbent layer, see dotted line 223 in FIG. 9B, which illustrates the path of a fold line extending beyond the rear end of the first and second portion. This improves surface coverage of the central chassis with the body of the wearer in the rear area towards the rear belt. Especially if the first and second portion do not overlap with the rear belt, such configuration is beneficial, given that at least a portion of the dotted shown in FIG. 9B will not be overlaid by the rear belt.

Moreover, the absorbent layer 117 is often not homogeneous outside the continuous channel. I.e. some areas of the absorbent layer have more absorbent material relative to other areas, leading to a profiled distribution of absorbent material.

The absorbent layer may comprise less absorbent material per surface area in the region towards the rear edge of the absorbent layer. For example, the area of the absorbent layer which is formed in 20% of the longitudinal dimension of the absorbent layer adjacent the rear edge of the absorbent layer, based on the total length of the absorbent layer as measured from the front edge to the rear edge along the longitudinal axis, may have less than 10%, or less than 8%, by weight of the total amount of absorbent material of the absorbent layer.

In such configurations, where the rear portion of the absorbent layer has relatively little amount of absorbent material, the absorbent core—and thus the central chassis as a whole—is more prone to bunching and folding. Therefore, it is especially beneficial to influence the formation of fold lines to some extent. As explained above, configuring the first and second portion in the claimed manner helps to facilitate the formation of folds beyond the rear end of the first and second portion such that the folds tend to form towards the longitudinally extending side edges of the absorbent layer.

Moreover, having the ratio of the first distance L1 to the second distance L2 being from 1.2 to 2.5, the ratio of the first transverse width W1 of the absorbent layer across the necking point of the first and second portion to the first distance L1 being higher than the ratio of the second transverse width W2 of the absorbent layer across the rear ends of the first and second portion to the second distance L2, results in a curvature of the first and second portion which provides improved body surface coverage and improved fit of the central chassis towards rear belt. As the second distance L2 between the first and second portion at the portions' rear ends is substantially wider than the first distance L1 at the portions' necking point, the absorbent core, and thus of the central chassis, stays wider and, overall, can reduce the inboard folding of the central chassis. This leads to wider, better body surface coverage at the buttocks of the wearer, and increases of comfort and fit.

The first and second portion 126, 226 are spaced apart from each other at their front ends 215 by a third distance L3. The third distance L3 is measured between the middle of the first portion 126 at the first portion's front end and the middle of the second portion 226 at the second portion's front end. The third distance L3 may be from 48 mm to 70 mm, or from 50 mm to 65 mm, or from 50 mm to 60 mm. The third distance L3 may be larger than the first distance L1. The third distance L3 may be equal to the second distance L2. Alternatively, L2 and L3 may not differ from each other by more than 30%, or not more than 20%, or not more than 10%, or not more than 5% based on the longer distance.

The absorbent layer 117 has a third transverse width W3 measured from the first longitudinally extending side edge to the second longitudinally extending side edge of the absorbent layer across the front ends 215 of the first and second portion 126, 226. The third transverse width W3 may be from 50 mm to 150 mm, or from 50 mm to 130 mm, or from 50 mm to 115 mm, or from 60 mm to 115 mm, or from 80 to 115 mm. The third transverse with W3 may be equal to or may be wider than the first transverse width W1. The third transverse width W3 may be equal to, smaller than, or larger than the second transverse width W2.

The ratio of the third transverse width W3 to the third distance L3 may be from 1.5 to 2.8.

The ratio of the first transverse width W1 to the first distance L1 may be higher than the ratio of the third transverse width W3 to the third distance L3.

The ratio of L3 to L1 may be from 1.2 to 2.5, or from 1.4 to 2.2, or from 1.5 to 2.0.

If the ratio of the third transverse width W3 to the third distance L3 is from 1.5 to 2.8, the ratio of the third length L3 to first length L1 is from 1.2 to 2.5 and the ratio of W1 to L1 is higher than the ratio of W3 to L3, this provides an absorbent layer wherein the portions are configured such that the central chassis of disposable absorbent pant has a further improved fit.

Moreover, if the ratio between the first distance L1 and the third distance L3 is from 1.2 to 2.5, and, further, if the ratio of the first transverse width W1 of the absorbent layer across necking point of the first and second portion to the first distance L1 is higher than the ratio of the third transverse width W3 of the absorbent layer across the front ends of the first and second portion to the third distance L3, this provides a curvature of the first and second portion which can improve body surface coverage and fit of the central chassis towards the front belt. If the third distance L3 between the first and second portion at the portions' rear ends is substantially wider than the first distance L1 at the portions' necking point, the absorbent core, and thus of the central chassis, stays wider and, overall, can reduce the inboard folding of the central chassis. This leads to wider body surface coverage towards the front waist region of the wearer, thus increase comfort and fit.

The third distance L3 between the front end 215 of the first portion 126 and front end 215 of the second portion is larger than the distance between any two points located on the third portion. The second distance L2 between the rear end 216 of the first portion 126 and the rear end 216 of the second portion is larger than the distance between any two points located on the fourth portion. The second and third distances L2 and L3 are each larger than the distance between any two points located on the first and second portion between the front and rear ends of the first and second portion.

The front end 215 of the first and second portion 126, 226 may be closer to the lateral axis x than any point on the third portion 127 (as exemplarily shown in FIGS. 7, 8, 9, 11A, 11B and 12). No point on the third portion may be spaced by a wider distance from the lateral axis x than the center of the third portion. The center of the third portion may be spaced away from the lateral axis x by a larger distance than any other point on the third portion.

The rear end 216 of the first and second portion 126, 226 may be closer to the lateral axis x than any point on the fourth portion 227 (as exemplarily shown in FIGS. 7, 8, 9, 11A, 11B and 12). No point on the fourth portion may be spaced at a wider distance from the lateral axis x than the center of the fourth portion. The center of the fourth portion may be spaced away from the lateral axis x by a larger distance than any other point on the fourth portion.

By having the laterally-extending elongate third and fourth portion extending between the first and second portion, the bending and flexing of the absorbent layer and of the center chassis as a whole can be improved to assist a close contact between the center chassis and the body of the wearer. The third and fourth portions, similar to the first and second portion, can act as hinges which ease bending and flexing of the center chassis to follow the contour of the wearer's body.

The first, second, third and fourth portion of the continuous channel may each have a width we of at least 3 mm, or from 3 mm to 15 mm, or from 5 mm to 12 mm, or from 5 mm to 10 mm as measured along the shortest path from the first to the second longitudinal edge of the first and second portion, respectively, and as measured along the shortest path from the first to the second lateral edge of the third and fourth portion, respectively. The width may be the same along each of the first, second, third and fourth portion. Alternatively, the width may vary across the length of the first, second, third and fourth portion, e.g. the width may vary from 3 mm to 15 mm, or from 5 mm to 12 mm, with the average width being from 5 to 10 mm. The width of the first, second, third and fourth portion, like all other dimensions and ratios provided herein, are to be measured on a dry product.

The average width of each of the first, second, third and fourth portion may be from 3% to 15%, or from 4% to 12%, or from 5% to 10% of the width of the absorbent layer (if the absorbent layer does not have constant width, i.e. if it does not have a rectangular shape, the width to be taken into account is the average width of the absorbent layer as measured in those areas of the absorbent layer which are provided with continuous channel. I.e. areas towards the front and rear edges 119 and 219 of the absorbent layer, where the continuous channel is provided, are not taken into account for calculating the average width of the absorbent layer.

The continuous channel may be permanent. By permanent, it is meant that the integrity of the continuous channel is substantially maintained both in dry state and wet state, i.e. the configuration of the continuous channel is substantially resistant to the effects of wetting, and substantially withstand mechanical stresses in the materials caused by swelling of superabsorbent polymer particles, pressure within the structure resulting therefrom, and the wearer's body movements. However, the permanent continuous channel may reduce in width we upon wetting due to swelling of the absorbent material (such as superabsorbent polymer particles) which are provided along the inner and outer boundary of the continuous channel.

A permanent continuous channel may be formed by immobilizing the superabsorbent polymer particles on a substrate layer, such as by applying a hot-melt adhesive material over the absorbent layer.

The absorbent layer may be provided between a first substrate layer 116 positioned towards the backsheet of the central chassis, and a second substrate layer 116' positioned towards the topsheet of the central chassis. The first and second substrate layer may each comprise or consist of a nonwoven web.

The continuous channel may be formed as a permanent channel by permanently bonding of the first substrate layer and the second substrate layer together along the continuous channel, thereby forming areas that separate and contain superabsorbent polymer particle deposits (and other absorbent material, if present in the absorbent layer) and thereby define the continuous channel therethrough (in the thickness direction). Adhesive may be used to bond (e.g. by direct bonding with no additional materials provided between the first and second substrate layer in the bonded area except for the adhesive) the first and second substrate layers 116, 116' together along the continuous channel, but it is possible to directly bond the substrate layers together (e.g. by direct bonding with no additional materials provided between the first and second substrate layer in the bonded area except for a possible adhesive) via other means, for example, ultrasonic bonding, pressure bonding, thermal bonding or combinations thereof (including combinations with adhesive bonding). The first and second substrate layer may be continuously bonded or intermittently bonded along the continuous channel.

The first and second portion 126, 226 located in the absorbent layer 117 may divide the absorbent layer into three sections at least in the crotch region 123. As exemplified in FIGS. 2A, 2B and 8, the first and second portions may be present in the crotch region of the absorbent layer. The first and second portions may extend, as measured along the longitudinal axis y along a straight line from the portion front end 215 to the portion rear end 216, longitudinally along from 30% to 70%, or from 35% to 65%, or from 40% to 65%, or from 45% to 60% of the total length of the absorbent layer, as measured along the longitudinal axis y from the front edge 119 to the rear edge 219. The first and second portion may be present only in the crotch region 123.

The third portion 127 and may be present in the crotch region, or may be present in the front waist portion, or a part of the third portion may be present in the crotch region while the remaining part of the third portion is present in the front waist portion.

Likewise, the fourth portion 227 and may be present in the crotch region, or may be present in the rear waist portion, or a part of the fourth portion may be present in the crotch region while the remaining part of the fourth portion is present in the rear waist portion.

When present only in the crotch region, the first and second portion may extend over the whole longitudinal dimension of the crotch region, or, if the first and second portion are shorter in longitudinal length than the crotch region, they may extend in only part of the crotch region. The first and second portion 126, 226 may be present in the crotch region, or part thereof, and part of the front waist region and/or part of the rear waist region. The first and second portion may be present in the front waist and crotch regions, i.e. the two portions extend from the crotch region (or part thereof) into the front waist region. The first and second portion may be present in the rear waist region and crotch regions, i.e. the portions extend from the crotch region (or part thereof) into the back region.

The first and second portion 126, 226 may be mirror images of one another with respect to the longitudinal axis y of the absorbent layer 117.

It is desired that the continuous channel 100 does not extend all the way to the laterally extending front edge 119 and rear edge 219 of the absorbent layer 117. The absorbent layer may include, along each laterally extending edge and adjacent to said edge, a so-called "end deposit" of absorbent material, such as superabsorbent polymer particles, which is free of the continuous channel.

Adjacent to the laterally extending front edge 119 of the absorbent layer 117, such end deposits may have a respective length which is from 5% to 25%, or from 5% to 20%, or from 10% to 20% of the longitudinal dimension of the absorbent layer as measured along the longitudinal axis from the front edge 119 to the point of the continuous channel 100 which is closest to the front edge 119. In other words, the continuous channel 100 terminates from 5% to 25%, or from 5% to 20%, or from 10% to 20% longitudinally inboard (i.e. towards the transverse axis) from the front edge 119 of the absorbent layer.

Adjacent to the laterally extending rear edge 219 of the absorbent layer 117, such end deposits may have a respective length which is from 10% to 45%, or from 15% to 40%, or from 20% to 40% of the longitudinal dimension of the absorbent layer as measured along the longitudinal axis from the rear edge 219 to the point of the continuous channel 100 which is closest to the rear edge 219. In other words, the continuous channel 100 terminates from 10% to 45%, or from 15% to 40%, or from 20% to 40% longitudinally inboard (i.e. towards the transverse axis) from the rear edge 216 of the absorbent layer.

The front end 215 of each of the first and second portion 126, 226 may be closer towards the front edge 119 of the absorbent layer than the rear end 216 is towards the rear edge 219 of the absorbent layer. The continuous channel 100 (as a whole) may be closer towards the front edge 119 of the absorbent layer than towards the rear edge 219 of the absorbent layer. Thus, the continuous channel 100 may be spaced at a wider distance from the rear edge of the absorbent layer than from the front edge of the absorbent layer.

Furthermore, in order to reduce the risk of fluid leakage and run-off, it may be desired that the continuous channel does not extend to the first and second longitudinal side edges 118, 218 of the absorbent layer 117. The absorbent layer may include, along each of the first and second longitudinally extending side edge 118, 218 and adjacent to said edge, a deposit of absorbent material, such as superabsorbent polymer particles, free of the continuous channel (and free of any other channels, if present in the absorbent layer).

The first portion 126 is provided between the longitudinal axis y and the first side edge 118 of the absorbent layer 117. The second portion 226 is provided between the longitudinal axis y and the second side edge 218 of the absorbent layer.

Each of the first and second portion 126, 226 is curved such that the portion's necking point 220 is closer to the longitudinal axis y than the first and second portion's front and rear ends 215, 216.

Longitudinally extended and curved first and second portions can serve as hinge structures in the absorbent core which help enable the absorbent core to flex longitudinally and thereby conform to the wearer's anatomy along the transverse direction in the crotch region and towards/in the front and rear waist regions. Thus, the first and second portions may contribute to imparting a comfortable and superior fit in addition to permitting improved liquid transportation and distribution. However, as described above, such flexing and folding along the first and second portions can also have certain disadvantages when used in pants as the absorbent core may fold into a U-shape which can be too narrow if not configured in accordance with the present invention, leading in fact to reduced contact of the central chassis and the body of the wearer and bunching of the absorbent core in the crotch and towards the front and rear waist region.

The longitudinally-oriented first and second portion of the continuous channel formed in the absorbent layer may help transport and distribute liquid (e.g., urine) along the lengths of the deposits of absorbent material, such as superabsorbent polymer particles, in the absorbent layer, and thereby help speed acquisition and absorption. However, the correspondingly-defined longitudinal areas containing or defining the deposits of superabsorbent polymer particles may develop elevated internal pressure as the particles absorb liquid, swell, and press against each other. This pressure may have a longitudinal, structural stiffening effect on the absorbent core. The internal pressure causes the absorbent layer to tend to straighten longitudinally, rather than easily curve around and beneath the wearer's lower torso as the absorbent core wraps between the wearer's legs.

Figure 10A:
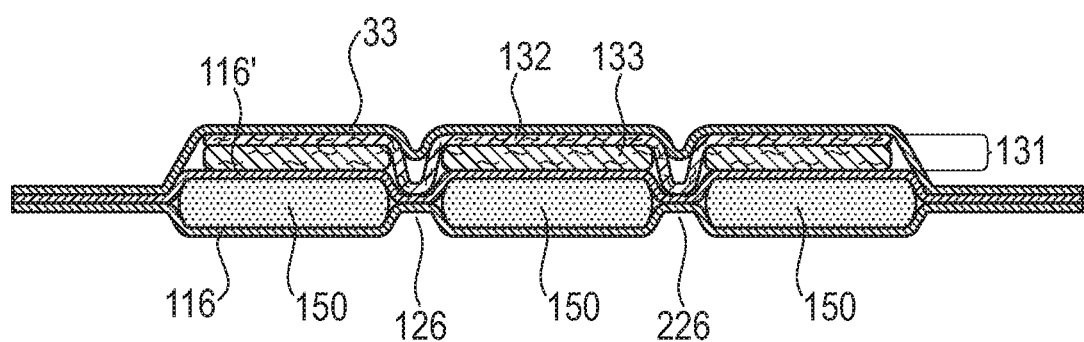
FIG. 10A is a schematic lateral cross-section view of a central chassis through the first and second portion.
Figure 10B:
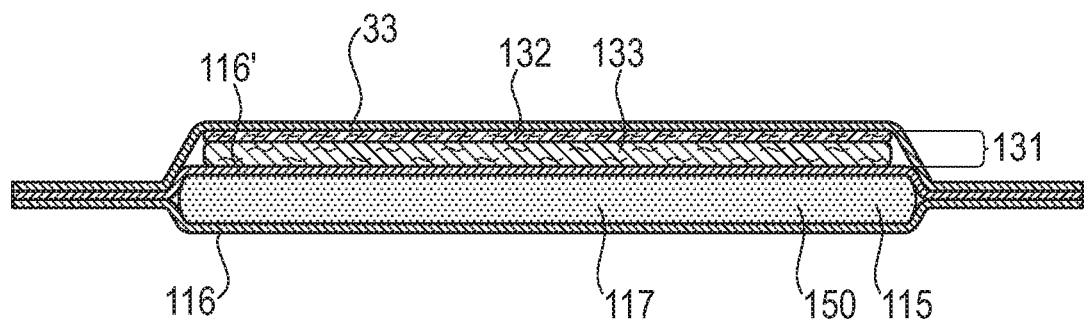
FIG. 10B is a schematic lateral cross-section view of a main chassis outside the continuous channel.

The continuous channel 100 imparted in the absorbent layer 117, or parts of the continuous channel, such as the first and second portion, may be non-permanent. This enables the absorbent core to change from a first configuration when dry to a second configuration when wetted to, e.g., one-quarter, one-third, one-half, two-thirds or more of the total absorbent capacity (by weight of absorbed liquid) of the absorbent layer. For example, means or materials, such as a pressure bond or an adhesive, bonding the first substrate layer 116 to the second substrate layer 116' to form the continuous channel 100 may be configured to change structure when wetted. As illustrated in FIGS. 10A and 10B, an absorbent core 115 may have a first configuration when dry (e.g., FIG. 10A) and a second configuration when wetted (e.g., FIG. 10B), e.g. to more than half of its absorbent capacity. One mechanism that may be used to enable this may be a water soluble or otherwise releasable adhesive affixing the first and second substrate layer 116 and 116' together along, and thereby defining, the continuous channel 100. Upon wetting and/or upon outward pressure against the first and second substrate layers 116 and 116' from the swelling deposits of superabsorbent polymer particles, the adhesive releases, and the swelling deposits of superabsorbent polymer particles are permitted to expand into the volume previously defined by (i.e. surrounding) the continuous channel 100, which then may reduce in size or even disappear as suggested in FIG. 10B. This may have the effect of relieving pressure within the absorbent layer 117 and absorbent core 115, which may lessen the longitudinal stiffening effects described above. Thus, certain advantages of the continuous channel (flexibility, conformability and liquid distribution enhancement) may be enjoyed at times before the central chassis is substantially wetted, while a possible disadvantage of channel (longitudinal stiffness) may be mitigated at times after the pant has been substantially wetted.

The longitudinal dimension of each of the first and second portion 126, 226 may be notionally divided into three, four, five or more sub-lengths (i.e. subsections). Each subsection may represent at least 10%, or at least 20% of the total length of each of the first and second portion as measured along the longitudinal axis. The absorbent layer having the first and second portion provided therein, may be configured to permanently define the first and second portion along one or more of the sub-lengths, but to changeably define the portions along other of the sub-lengths, such that they reduce in size or disappear upon wetting.

Figure 11C:
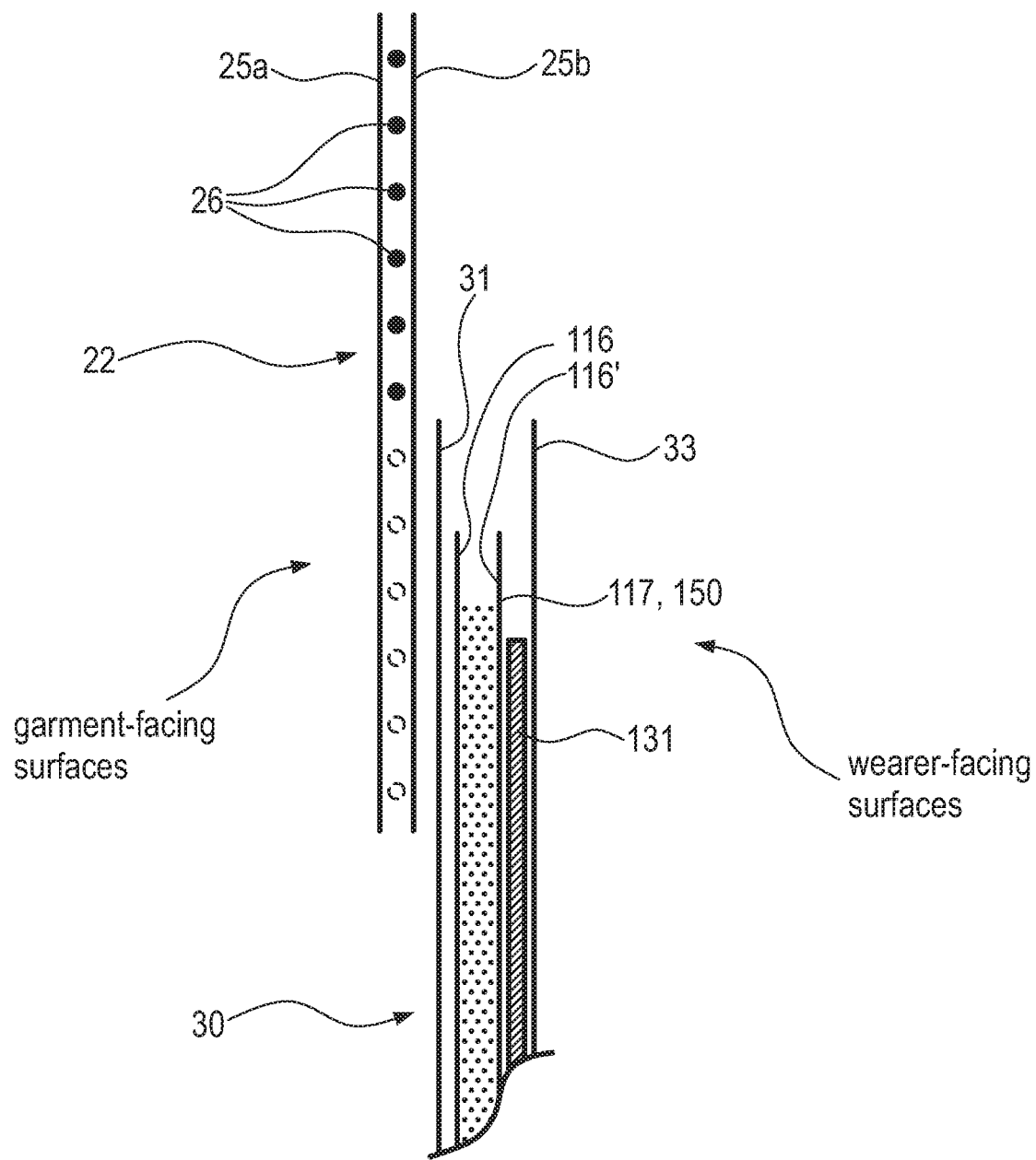
FIG. 11C is a schematic, exploded longitudinal cross section view of a portion of the disposable absorbent pant depicted in FIG. 11A.

The absorbent layer 117 may extend longitudinally such that the third portion 127, the front end 215 of the first and second portion, or both, i.e. the third portion and the front end of the first and second channel are disposed in an overlapping configuration with the front belt 22. In that way, the parts of the continuous channel are disposed beneath the front belt (i.e. closer to the body of the wearer) when the pant is worn. Non-limiting examples are suggested in FIGS. 11A-11C. Alternatively or in addition, the absorbent layer 117 may extend longitudinally such that the fourth portion 227, the rear end 216 of the first and second portion, or both, i.e. the fourth portion and the rear end of the first and second channel are disposed in an overlapping configuration with the rear belt 23. In that way, parts of the continuous channel are disposed beneath the rear belt (i.e. closer to the body of the wearer) when the pant is worn. However, it may be preferred that the first and second portion do not overlap with the rear belt 23. It may also be preferred that the fourth portion does not overlap with the rear belt, such that the continuous channels does not overlap with the rear belt at all.

The absorbent layer, absorbent structure and/or configuration of channels may also have any features described in U.S. Pat. App. Pub. Nos. US2014/0163511; US2014/0163503; US2014/0163501; US2014/0163500; US2012/0316526; US2012/0316528; US2014/0163501; and US2014/0371701.

Absorbent Layer

The absorbent layer may include superabsorbent polymer particles 150 alone or in combination with other materials, such as cellulose fibers. The superabsorbent polymer particles may be immobilized on the first and/or second substrate layer 116, 116' by, for example, a hot-melt adhesive material. Absorbent polymer particles suitable for use in the absorbent layer may include any superabsorbent polymer particles known from superabsorbent literature, for example such as described in Modern Superabsorbent Polymer Technology, F. L. Buchholz, A. T. Graham, Wiley 1998.

The superabsorbent polymer particles may be spherical, spherical-like, ellipsoid, or irregularly shaped, such as ovoid-shaped particles of the kind that may be obtained from inverse phase suspension polymerizations. The particles may, optionally, be agglomerated at least to some extent to form larger irregular agglomerations of particles.

The superabsorbent polymer particles may be selected from among polyacrylates and polyacrylate based materials that are internally and/or surface cross-linked, such as for example partially neutralized cross-linked polyacrylates or acid polyacrylate. Examples of absorbent polymer particles suitable in the present disclosure are described for instance in the PCT Pat. App. Nos. WO07/047598, WO 07/046052, WO2009/155265 and WO2009/155264.

The absorbent layer may be substantially cellulose-free (also referred to as "airfelt"). "Substantially" cellulose-free, as used herein, means that the absorbent layer comprises less than 10% by weight, or less than 5% by weight, or less than 2% by weight, or less than 1% by weight of cellulose, or no cellulose (i.e. 0% by weight) based on the total weight of absorbent material in the absorbent layer. Cellulose fibers have been used as absorbent material in absorbent cores of disposable diapers. Such fibers possess absorbent properties and imparts some absorption capacity to an absorbent layer, but also may be included to provide a structural matrix to hold dispersed particles of superabsorbent polymer particles. While inclusion of such superabsorbent polymer particles enhances absorption capacity, keeping such particles suitably dispersed may be important to prevent the particles from "gel-blocking" in use as they swell with absorbed liquid and block the passageways therebetween which allow liquid to move through deposits thereof, compromising absorption capacity. The inclusion of cellulose fibers ("airfelt") as a matrix for superabsorbent polymer particles can serve to reduce or prevent gel-blocking. However, it also imparts bulk to an absorbent layer, even before absorption of any liquids. To reduce the overall size and/or thickness of the absorbent layer, and thereby improve wearer comfort and reduce the bulkiness of the pant for purposes of packaging and shipping volume efficiency, it may be desired to construct an absorbent core using the lowest volumes of core materials possible within performance constraints. Toward this end, examples of suitable materials and constructions for a suitable absorbent structure are described in, but are not limited to WO2008/155699. Generally, these applications describe absorbent layer constructions that minimize or eliminate the need for and inclusion of airfelt in combination with particles of superabsorbent polymer particles ("substantially cellulose-free" structures). Suitable methods for forming deposits of absorbent superabsorbent polymer particles are additionally disclosed in, for example, EP 1621167 A2, EP 1913914 A2 and EP 2238953 A2.

If the absorbent core 115 comprises a first and second substrate layer 116, 116' with the absorbent layer 117 provided in between, the absorbent material, such as the superabsorbent polymer particles, may be immobilized on one or both of the first and second substrate layer.

Immobilization may be achieved by applying a hot-melt adhesive material, which holds and immobilizes the absorbent material, such as the superabsorbent polymer particles (and cellulose fibers when present), on the first and/or second substrate layer. Some hot-melt adhesive material may also penetrate into the layer of absorbent material, such as the layer of superabsorbent polymer particles, and into the first and/or second substrate layer to provide further immobilization and affixation. The hot-melt adhesive material may not only help in immobilizing the absorbent material, such as the superabsorbent polymer particles, on the substrate layer but also may help in maintaining the integrity of the continuous channel. The hot-melt adhesive material avoids that a significant amount of absorbent material, such as superabsorbent polymer particles, migrates into the continuous channel.

Hot-melt adhesive materials suitable for use in the present disclosure may include at least a thermoplastic polymer in combination with a plasticizer and other thermoplastic diluents such as tackifying resins and additives such as antioxidants.

Example suitable hot melt adhesive materials are described in EP 1447067 A2.

Acquisition/Distribution System

The central chassis 30 may comprise an acquisition/distribution system (ADS) 131, which is disposed between the absorbent core 115 and the topsheet 33. The acquisition/distribution system may serve as a temporary reservoir for liquid until the absorbent core can absorb the liquid, and for subsequent distribution of the liquid into the absorbent core in an efficient manner. The acquisition/distribution system may consist of a single layer or comprise multiple layers, such as an upper layer 132 provided adjacent to the topsheet 33 and facing towards the wearer's skin, and a lower layer 133 provided adjacent to the absorbent core 115 and facing the garment of the wearer. The acquisition/distribution system may be in direct contact with the absorbent core.

The ADS 131 may be free of superabsorbent polymer. The prior art discloses many types of acquisition-distribution systems, see for example WO2000/59430, WO95/10996, U.S. Pat. No. 5,700,254, WO02/067809.

The function of a lower layer 133 is typically to spread the insulting fluid liquid over a larger surface within the central chassis so that the absorbent capacity of the absorbent core can be more efficiently used. The lower layer 133 may be made of a nonwoven material based on synthetic or cellulosic fibers and having a relatively low density. The lower layer may typically have an average basis weight of from 30 to 400 $g/m^2$, in particular from 80 to 300 $g/m^2$. The lower layer may not be formed of a coherent, self-sustaining web or sheet but may be a layer with little integrity on its own.

The lower layer 133 may for example comprise at least 50%, or 60%, or 70%, or 80%, or 90% by weight of cross-linked cellulose fibers. The cross-linked cellulosic fibers may be crimped, twisted, or curled, or a combination thereof including crimped, twisted, and curled. The cross-linked cellulosic fibers provide higher resilience and therefore higher resistance to the first absorbent layer against the compression in the product packaging or in use conditions, e.g. under baby weight. This provides the central chassis with a relatively high void volume, permeability and liquid absorption, and hence reduced leakage and improved dryness.

The lower layer 133 comprising cross-linked cellulose fibers, may comprise other fibers, but this layer may advantageously comprise at least 50%, or 60%, or 70%, or 80%, or 90% or even up to 100%, by weight of the layer, of cross-linked cellulose fibers. Examples of such mixed layer of cross-linked cellulose fibers may comprise 70% by weight of chemically cross-linked cellulose fibers, 10% by weight polyester (PET) fibers, and 20% by weight untreated pulp fibers. In another example, the layer of cross-linked cellulose fibers may comprise 70% by weight chemically cross-linked cellulose fibers, 20% by weight lyocell fibers, and 10% by weight PET fibers. In another example, the layer may comprise 68% by weight chemically cross-linked cellulose fibers, 16% by weight untreated pulp fibers, and 16% by weight PET fibers.

The central chassis 30 may further comprise an upper layer 132, whose function is typically to quickly acquire the fluid away from the topsheet so as to provide a good dryness for the wearer. The upper layer 132 is typically placed directly under the topsheet and directly above the lower layer 133. The upper layer 132 may typically be or comprise a non-woven material, for example a SMS or SMMS material, comprising two outer spunbonded (S) layers with one or more melt-blown (M) layers in between, or alternatively a carded chemical-bonded nonwoven. The non-woven material may, in particular, be latex bonded. Exemplary upper layers 132 are disclosed in U.S. Pat. No. 7,786,341. Carded, resin-bonded nonwovens may be used, in particular where the fibers used are solid round or round and hollow PET staple fibers (such as a 50/50 or 40/60 mix of 6 denier and 9 denier fibers).

A carded resin-bonded upper layer 132 may be stabilized by a latex binder, for example a styrene-butadiene latex binder (SB latex). Processes for obtaining such lattices are known, for example, from EP 149 880 (Kwok) and US 2003/0105190 (Diehl et al). The binder may be present in the upper layer 132 in excess of 15%, or of 20% by weight, but may be present by not more than 40%, or not more than 35% by weight of the upper layer 132. SB latex is, for example, available under the trade name GENFLO™ 3160 (OMNOVA Solutions Inc.; Akron, Ohio).

A further layer may be used in the ADS 131 in addition to upper and lower layer 132 and 133 described above. For example, a wet-laid cellulose layer (so-called tissue) may be placed between the upper and lower layer 132 and 133 or between the lower layer 133 and the absorbent core 115. The tissue and the upper layer 132 may be of the same size or may be of different size, for example the tissue may extend further in the back of the central chassis 133 than the upper layer. An example of hydrophilic tissue is a 13-15 g/m² high wet strength tissue from supplier Havix. However, the ADS may only consist of the upper and the lower layer 132 and 133.

One or more of the layers of the ADS may have elongated longitudinally extending first and second openings 141 and 142, each opening having a front opening end and a rear opening end. The first and second opening may be congruent with the first and second portion 126, 226 of the continuous channel in the absorbent layer (i.e. the first opening is congruent with the first portion and the second opening is congruent with the second portion), while the first or second opening may each be shorter than the first and second portion in longitudinal dimension. Consequently, the front opening end of the first and second opening 141 and 142 may be longitudinally offset from the front end 215 of the first and second portion 126 and 226, respectively. Thus, the front opening end of the first and second opening may be closer to the transverse axis x than the front end of the first and second portion. Alternatively, or in addition to the offset of the front end of the first and second openings relative to the front end of the first and second portion, the rear opening end of the first and second opening 141 and 142 may be longitudinally offset from the rear end 216 of the first and second portion 126 and 226, respectively. Thus, the rear opening end of the first and second opening may be closer to the transverse axis x than the rear end of the first and second portion.

Alternatively, one or more of the layers of the ADS may have a continuous opening which is congruent with the continuous channel 100 in the absorbent layer.

In one configuration, the ADS may have an upper and a lower layer 132 and 133. The first and second opening 141 and 142 described above or the continuous opening described above may be provided in the upper and the lower layer. However, it may be desirable to provide the first and second opening 141 and 142 or the continuous opening in the lower layer 133 while leaving the upper layer 132 free of openings. The upper layer 132 may be directly attached to the absorbent core 115, e.g. to the second substrate layer 116' of the absorbent core 115, through the first and second opening or the continuous opening in the lower layer 133. This direct attachment may be facilitated by adhesive bonding, pressure bonding, heat bonding, ultrasonic bonding, or combinations thereof.

By attaching the upper layer 132 to the absorbent core through the first and second opening 141 and 142 or through the continuous opening of the lower layer 133, the lower layer is held in position, also during use of the absorbent article. The lower layer 133 may be formed of fibers which are not consolidated into a coherent web or sheet, e.g. by air laying the fibers of the lower layer 133 without subsequently bonding the each other. In such configurations, the material of the lower layer may be more prone to shifting and moving out of place, especially during use and after the central chassis has been wetted with urine or other liquid. Therefore, attaching the upper layer to the absorbent core through the first and second openings or through the continuous opening of the lower layer is especially beneficial.

Also, by having the first and second portion being largely congruent with the first and second opening (as said, the first and second opening may be shorter than the first and second portion) or by having the continuous channel being congruent with the continuous opening further improves transport and distribute liquid (e.g., urine) to the absorbent core and along the lengths of the deposits of absorbent material, such as superabsorbent polymer particles, in the absorbent layer, and thereby help speed acquisition and absorption.

First and Second Elasticized Belt

The disposable absorbent pant of the present invention comprises an elasticized front belt 22 provided in the front waist region and an elasticized rear belt 23 provided in the rear waist region. The front and rear belt 22 and 23 each have a body-facing surface and a garment-facing surface. The body-facing surface will face towards the skin of the wearer in use of the disposable pant and the garment-facing surface will face away from the skin of the wearer during use of the disposable pant and towards the garment of the wearer.

The front belt 22 has a transversally extending front waist edge 34 and the rear belt 23 has a transversally extending rear waist edge 35. The front and rear belt 22 and 23 each have a first and second longitudinally extending side edge 230 and 231. The first side edge 230 of the front belt 22 is joined to the first side edge 230 of the rear belt 23 and the second side edge (231) of the front belt (22) is joined to the second side edge 231 of the rear belt 23 at side seams 24 to form a waist opening and two leg openings 15. The waist opening is formed in conjunction by the front and rear waist edge.

Each of the front and rear belt 22 and 23 may be formed of an inner layer 25a, an outer layer 25b and a plurality of elastic members 26, such as elastic strands, disposed between the inner layer and the outer layer. The plurality of elastic members, may be provided such that they extend in transverse direction and the individual elastic members are longitudinally spaced apart from each other.

The pant may have the front and rear belt 22 and 23 being longitudinally separated from each other such that there is a gap between the front and rear belt along the longitudinal axis y and the central chassis 30 is provided in between the front and rear belt 22 and 23 along the longitudinal axis y. In such configurations, the central chassis 30 overlaps the front and rear belt 22 and 23 and is attached to the front belt 22 in the overlapping regions, i.e. along and/or adjacent the central chassis' laterally extending chassis front edge 135 and attached to the rear belt 23 along and/or adjacent its laterally extending chassis rear edge 136. Attachment may be facilitated by adhesive bonding, pressure bonding, heat bonding, ultrasonic bonding, or combinations thereof. Further, in such configurations, the central chassis is attached to the body-facing surface of the front and rear belt 22 and 23. In such configurations, the elasticized front belt 22 has a first transversally extending first lower edge 18 disposed between the front waist edge 34 and the lateral axis x, and the elasticized rear belt 23 has a transversally extending second lower edge 19, disposed between the rear waist edge 35 and the lateral axis x. If the front and rear belt 22 and 23 comprise an inner and an outer layer, the first and second lower edges 21 may be formed by one or both of the inner and outer layers.

The pant has an overall length L4 as measured from the front waist edge 34 to the rear waist edge 35 along the longitudinal axis y. The overall length L4 is measured prior to attaching the front and rear belt to each other along side seams 24, or after the side seams have been torn open, and the pant has been stretched out flat on an even surface, such as a table.

For pants having the front and rear belt not extending through the crotch region but having a first transversally extending first lower edge 18 at the front belt and a second lower edge 19 at the rear belt, the crotch region is defined in between the first and second lower edge 18 and 19 along the longitudinal axis y. I.e. the crotch region is formed by those portions of the central chassis which do not overlap with the front or rear belt. In such pants, the pant has a crotch region length L5 as measured from the first lower edge 18 of the front belt to the second lower edge 19 of the rear belt.

If the first and/or second lower edge 18 and 19 are not parallel to the transverse axis x, the crotch region length L5 is measured at the longitudinal axis.

In order to improve proper fit of the pant, especially in the crotch region, the ratio of the overall length L4 to the crotch region length L5 may be from 1.9 to 2.6, or from 2.0 to 2.5. Such ratios ensure that the crotch region has an appropriate length versus the overall length L4 of the disposable pant, thus helping a close contact of the central chassis to the body of the wearer in the crotch region and good positioning of the front and rear belt across the waist, hips, belly and back of the wearer for improved fit.

The absorbent layer 117 of the absorbent core 115 may overlap with the front and rear belt.

The rear end 216 of each of the first and second portion 126, 226 of the continuous channel 100 may not overlap with the rear belt 23. In addition, also the fourth portion 227 of the continuous channel 100 may not overlap with the rear belt 23. Thereby, the first and second portions cannot act as hinges or fold lines in the area of the absorbent layer, which overlaps the rear belt. Consequently, the transversally extending elastic members are not contracted by the pulling forces of an absorbent layer which folds along the first and second portion of the continuous channel. The rear end 216 may be spaced away (towards the transverse axis x) from the second lower edge 19 by from 5 mm to 25 mm, or from 10 mm to 20 mm. This range has been found advantageous irrespective of the overall length L5 of the crotch region. The crotch region length L5 may be from 170 mm to 250 mm. By this spaced configuration, the surface coverage of the skin at the buttocks of the wearer is improved. Due to the offset of the first and second portion's rear end from the second lower edge 19, the U-shaped folding which the absorbent core—and the central chassis as a whole—tends to adopt upon pulling up the disposable pants to put the pant in place on the wearer, stops at a distance below the second lower edge 19, thereby helping to properly fit the central chassis beneath the rear belt on the skin of the wearer without any undesired and uncomfortable bunching and folding of the central chassis beneath the rear belt.

The front end 215 of each of the first and second portion 126, 226—and consequently also the third portion 127— may overlap with the front belt 22. Alternatively, only the third portion, or a part thereof, may overlap with the front belt 22 while the front end 215 of each of the first and second portion 126, 226, does not overlap with the front belt 22. Given that the body surface of the wearer is typically smaller in the area where the crotch region migrates to the belly of the wearer, and thus at the lower portion of the front belt compared to the buttocks area, folding along the front ends 215 of each of the first and second portion does not negatively impact fit but rather can help to facilitate snug fit on the wearer, also when the front ends 215 overlap with the front belt. The front end 215 of each of the first and second portion may overlap the front belt by from 3 mm to 25 mm, or from 5 mm to 20 mm.

Alternatively to the disposable pant configuration described above, the front and rear belt may extend into the crotch region such that the pant does not have a first and second lower edge 18 and 19. In such pants, the central chassis will be covered by one or more layers of the front and rear belt 22 and 23 across the complete longitudinal dimension of the central chassis. One or more layers may continuously form the front and rear belt 22 and 23 in such configurations. For these kinds of disposable pants, the "crotch region" is the portion through which the lateral axis (herein, axis x) passes, and which extends longitudinally one-sixth of the overall length L4 of the pant frontward and rearward of the lateral axis. Accordingly, the front waist region includes the front one-third of the overall length L4 of the pant; the crotch region includes the middle one-third of the overall length L4 of the pant; and the rear waist region includes the rear one-third of the overall length L4 of the pant.

Referring e.g. to FIG. 12, elastic members such as elastic strands 26 may be configured within the front and/or rear belt such that they are present in lower side zones 22", 23"

(i.e. the zones lying left and right outside of a central zone 22' and 23' of the front and rear belt which is overlaid by the central chassis) of the front and rear belt, but not present in part or all of the lower central zones 22', 23' that overlie the central chassis 30. Thus, one or both belt may be configured such that one, more than one, or all of the layers that sandwich the elastic strands 26 are present in lower central zones 22', 23' of the front and rear belt 22, 23, such as nonwoven layers 25*a*, 25*b* (see FIG. 3), without elastic stretch enabled by the presence of pre-strained elastic members and ruffles of laterally gathered material. (Notably, in FIG. 3, "X" designates the lateral direction in general, not the lateral axis.) In the central zones 22', 23' that overlie the central chassis, the nonwoven layer(s) of one or both belts 22, 23 may be disposed and affixed to the central chassis material(s) (such as the backsheet) such that they overlie the central chassis in laterally extended condition, i.e., they do not have longitudinal ruffles or rugosities (e.g., ruffles or rugosities 27, illustrated in FIGS. 4 and 5) that would otherwise be imparted by lateral contraction of pre-strained, sandwiched lateral elastic strands. In this configuration, the fully extended belt layer material(s) overlying the central chassis 30 in lower central zones 22', 23', being without longitudinal ruffles and thereby being unable or less able to elastically stretch laterally as compared to the other elasticized, ruffled zones of the belt portions, are configured to provide greater resistance to lateral expansion, supplementing that of the central chassis materials and helping to support and restrain the ends of absorbent layer 117. This feature may be combined with any of the continuous channel configurations described above, for potentially synergistic effects in reducing folding and bulging of the absorbent layer 117 as described above.

PCT/CN2014/094890, which describes additional examples of belt configurations having non-elasticized portions overlying the chassis.

In a further example, one or more elastic strands 26 present in the lower side zones 22", 23" may be selected (e.g. by decitex and/or tensile modulus) and/or configured (e.g. by longitudinal numerical count/unit longitudinal dimension of the belt, and/or amount of imparted pre-strain) to impart greater tensile contractive force to the front and rear belt in one or more of the lower side zones 22", 23" than in the upper zone(s) closer to the waist edges. This latter example may help enhance comfort of the pant, when worn, by providing for relatively lesser lateral contractive tensile force about the waist band areas and waist edges, and relatively greater lateral contractive tensile force with greater support, resistance to bulging of the channeled absorbent layer, and anchoring of the pant about the wearer's lower hips. Thus, one or more of the elastic strands 26 in one or both of lower side zones 22", 23" may have one or more of greater decitex, greater tensile modulus, greater number of strands 26 per unit longitudinal length of the belt, or greater amount of pre-strain, than one or more of the elastic strands 26 in the upper zone(s) closer to the waist edges in the same front or rear belt. This feature may be incorporated alone, or in combination with, the inclusion of non-elasticized central zone(s) 22', 23' of the belt described immediately above.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular examples of the present invention have been illustrated and described, it would be obvious to those skilled in the art that various other changes and modifications may be made without departing from the spirit and scope of the invention. It is therefore intended to cover in the appended claims all such changes and modifications that are within the scope of this invention.

What is claimed is:

1. A disposable absorbent pant, having a longitudinal axis (y), a lateral axis (x), a front waist region, a rear waist region and a crotch region between the front and rear waist regions, the pant comprising:
   a central chassis extends from the front waist region through the crotch region to the rear waist region and comprises a topsheet, a backsheet and an absorbent core placed in between the topsheet and the backsheet, the central chassis having a laterally extending chassis front edge, a laterally extending chassis rear edge and first and second longitudinally extending chassis side edges;
   an elasticized front belt provided in the front waist region and an elasticized rear belt provided in the rear waist region, the front and rear belt each having a body-facing surface and a garment-facing surface, the front belt having a transversally extending front waist edge, the rear belt having a transversally extending rear waist edge, the front and rear belt each having a first and second longitudinally extending side edge, with the first side edge of the front belt being joined to the first side edge of the rear belt and the second side edge of the front belt being joined to the second side edge of the rear belt at side seams to form a waist opening and two leg openings;
   the absorbent core comprising an absorbent layer, the absorbent layer having a laterally extending front edge, a laterally extending rear edge and first and second longitudinally extending side edges, the absorbent layer comprising a continuous channel formed therein, the continuous channel having a first and a second longitudinally-oriented elongate portion and a third and fourth laterally-oriented elongate portion;
   the first portion being provided between the longitudinal axis (y) and the first side edge of the absorbent layer, the second portion being provided between the longitudinal axis (y) and the second side edge of the absorbent layer;
   the first and second portion each having a front end towards the absorbent layer's front edge, a rear end towards the absorbent layer's rear edge and a center which is equally spaced from the front and rear ends across the longitudinal axis (y), each of the first and second portion being curved such that the first portion is closer to the longitudinal axis (y) at a necking point than the front and rear end of the first portion, and such that the second portion is closer to the longitudinal axis (y) at a necking point than the front and rear end of the second portion;

the first and second portion being spaced apart from each other at their necking point by a first distance L1, wherein the distance L1 is from 20 mm to 50 mm;

the third portion connecting the front end of the first portion with the front end of the second portion and extending from the front end of the first portion to the front end of the second portion;

the fourth portion connecting the rear end of the first portion with the rear end of the second portion and extending from the rear end of the first portion to the rear end of the second portion;

the absorbent layer having a first transverse width W1 extending from the first longitudinally extending side edge to the second longitudinally extending side edge across the necking point of the first and second portion;

the first and second portion being spaced apart from each other at their rear ends by a second distance L2, the absorbent layer having a second transverse width W2 extending from the first longitudinally extending side edge to the second longitudinally extending side edge across the rear ends of the first and second portion;

the first and second portion being spaced apart from each other at their front ends by a third distance L3;

the third distance L3 between the front end of the first portion and front end of the second portion being larger than the distance between any two points located on the third portion;

the second distance L2 between the rear end of the first portion and the rear end of the second portion being larger than the distance between any two points located on the fourth portion;

the second and third distances L2 and L3 each being larger than the distance between any two points located on the first and second portion between the front and rear ends of the first and second portion;

wherein the ratio of W2 to L2 is from 1.5 to 2.8;

wherein the ratio of W1 to L1 is higher than the ratio of W2 to L2; and wherein the ratio of L2 to L1 is from 1.2 to 2.5; and wherein the necking point of the first portion is spaced from 5% to 30% away from the center of the first portion towards the rear end, based on the total length of the first portion, as measured along a straight line from the front end to the rear end of the first portion; and wherein the necking point of the second portion is spaced from 5% to 30% away from the center of the second portion towards the rear end, based on the total length of the second portion, as measured along a straight line from the front end to the rear end of the second portion.

2. The disposable absorbent pant of claim 1, wherein the first portion and the second portion are not closer to the longitudinal axis (y) at any other location than at their necking point.

3. The disposable absorbent pant of claim 1, wherein the absorbent layer comprises less than 10% by weight of absorbent material, based on the total amount of absorbent material in the absorbent layer, in an area extending from the rear edge of the absorbent layer towards the lateral axis (x) and spanning 20% of the longitudinal dimension of the absorbent layer, based on the total length of the absorbent layer as measured from the front edge to the rear edge of the absorbent layer along the longitudinal axis (y).

4. The disposable absorbent pant of claim 3, wherein L2 and L3 do not differ from each other by more than 30% based on the longer distance.

5. The disposable absorbent pant of claim 1, wherein the first and second portion are spaced apart from each other at their front ends by a third distance L3, the absorbent layer having a third transverse width W3 extending from the first longitudinally extending side edge to the second longitudinally extending side edge across the front ends of the first and second portion;

wherein the ratio of W3 to L3 is from 1.5 to 2.8;

wherein the ratio of W1 to L1 is higher than the ratio of W3 to L3; and wherein the ratio of L3 to L1 is from 1.2 to 2.5, or from 1.4 to 2.2, or from 1.5 to 2.0.

6. The disposable absorbent pant of claim 1, wherein the ratio of W1 to L1 is from 2.5 to 4.5.

7. The disposable absorbent pant of claim 1, wherein the elasticized front belt has a first transversally extending first lower edge disposed between the front waist edge and the lateral axis (x), and the elasticized rear belt has a transversally extending second lower edge, disposed between the rear waist edge and the lateral axis (x), and the central chassis is joined to the body-facing surface of the front belt adjacent to the chassis front edge and joined to the body-facing surface of the rear belt adjacent to the chassis rear edge.

8. The disposable absorbent pant of claim 7, wherein the disposable absorbent pant has an overall length L4 as measured from the front waist edge to the rear waist edge along the longitudinal axis (y), the pant further having a crotch region length L5 as measured from the first lower edge to the second lower edge, wherein the ratio of the overall length L4 to the crotch region length L5 is from 1.9 to 2.6; or from 2.0 to 2.5.

9. The disposable absorbent pant of claim 8, wherein the rear end of the first and second portion is spaced from the second lower edge by from 14 mm to 25 mm.

10. The disposable absorbent pant of claim 1, wherein the first transverse width W1 of the absorbent layer extending from the first longitudinally extending side edge to the second longitudinally extending side edge across the necking point of the first and second portion is from 50 mm to 150 mm.

11. The disposable absorbent pant of claim 1, wherein the first, second, third and fourth portions of the continuous channel have a width of from 5 to 12 mm, or from 5 mm to 10 mm.

12. The disposable absorbent pant of claim 1, wherein the first and second portion are substantially mirror images of each other with substantially no offset to each other along the longitudinal axis (y).

13. The disposable absorbent pant of claim 1, wherein the length of each of the first and second portion as measured along the longitudinal axis (y) is from 40% to 70%, or from 45% to 65%, or from 50% to 60% of the total length of the absorbent layer, the total length of the absorbent layer being measured along a straight line along the longitudinal axis (y) from the front edge to the rear edge of the absorbent layer.

14. The disposable absorbent pant of claim 1, wherein each belt has an inner layer, an outer layer and a plurality of elastic members disposed between the inner layer and the outer layer.

15. The disposable absorbent pant of claim 1, wherein the absorbent core comprises a first substrate layer, such as a nonwoven web, towards the backsheet and a second substrate layer, such as a nonwoven web, towards the topsheet, and absorbent material provided between first and second substrate layer, the absorbent material forming the absorbent layer.

16. The disposable absorbent pant of claim 15, wherein the first, second, third and fourth portions the continuous channel in the absorbent core are substantially free of absorbent material.

17. The disposable absorbent pant of claim 16, wherein the absorbent material comprises at least 90% of superabsorbent polymer particles by total weight of the absorbent material provided between the first and second substrate layer.

18. The disposable absorbent pant of claim 1, wherein the absorbent layer comprises superabsorbent polymer particles and cellulose fibers.

19. A disposable absorbent pant, having a longitudinal axis (y), a lateral axis (x), a front waist region, a rear waist region and a crotch region between the front and rear waist regions, the pant comprising:
- a central chassis extends from the front waist region through the crotch region to the rear waist region and comprises a topsheet, a backsheet and an absorbent core placed in between the topsheet and the backsheet, the central chassis having a laterally extending chassis front edge, a laterally extending chassis rear edge and first and second longitudinally extending chassis side edges;
- an elasticized front belt provided in the front waist region and an elasticized rear belt provided in the rear waist region, the front and rear belt each having a body-facing surface and a garment-facing surface, the front belt having a transversally extending front waist edge, the rear belt having a transversally extending rear waist edge, the front and rear belt each having a first and second longitudinally extending side edge, with the first side edge of the front belt being joined to the first side edge of the rear belt and the second side edge of the front belt being joined to the second side edge of the rear belt at side seams to form a waist opening and two leg openings;
- the absorbent core comprising an absorbent layer, the absorbent layer having a laterally extending front edge, a laterally extending rear edge and first and second longitudinally extending side edges, the absorbent layer comprising a continuous channel formed therein, the continuous channel having a first and a second longitudinally-oriented elongate portion and a third and fourth laterally-oriented elongate portion;
- the first portion being provided between the longitudinal axis (y) and the first side edge of the absorbent layer, the second portion being provided between the longitudinal axis (y) and the second side edge of the absorbent layer;
- the first and second portion each having a front end towards the absorbent layer's front edge, a rear end towards the absorbent layer's rear edge and a center which is equally spaced from the front and rear ends across the longitudinal axis (y), each of the first and second portion being curved such that the first portion is closer to the longitudinal axis (y) at a necking point than the front and rear end of the first portion, and such that the second portion is closer to the longitudinal axis (y) at a necking point than the front and rear end of the second portion;
- the first and second portion being spaced apart from each other at their necking point by a first distance L1, wherein the distance L1 is from 20 mm to 50 mm;
- the third portion connecting the front end of the first portion with the front end of the second portion and extending from the front end of the first portion to the front end of the second portion;
- the fourth portion connecting the rear end of the first portion with the rear end of the second portion and extending from the rear end of the first portion to the rear end of the second portion;
- the absorbent layer having a first transverse width W1 extending from the first longitudinally extending side edge to the second longitudinally extending side edge across the necking point of the first and second portion;
- the first and second portion being spaced apart from each other at their rear ends by a second distance L2, the absorbent layer having a second transverse width W2 extending from the first longitudinally extending side edge to the second longitudinally extending side edge across the rear ends of the first and second portion;
- the first and second portion being spaced apart from each other at their front ends by a third distance L3;
- the third distance L3 between the front end of the first portion and front end of the second portion being larger than the distance between any two points located on the third portion;
- the second distance L2 between the rear end of the first portion and the rear end of the second portion being larger than the distance between any two points located on the fourth portion;
- the second and third distances L2 and L3 each being larger than the distance between any two points located on the first and second portion between the front and rear ends of the first and second portion;
- wherein the ratio of W2 to L2 is from 1.5 to 2.8;
- wherein the ratio of W1 to L1 is higher than the ratio of W2 to L2; and
- wherein the ratio of L2 to L1 is from 1.2 to 2.5; and
- wherein the first portion follows a first curved path with only one curve between the necking point and the rear end of the first portion, and the first portion follows a second curved path with only one curve between the necking point and the front end of the first portion, wherein the first curved path of the first portion has a steeper curvature compared to the second curved path of the first portion; and
- wherein the second portion follows a first curved path with only one curve between the necking point and the rear end of the second portion, and the second portion follows a second curved path with only one curve between the necking point and the front end of the second portion, wherein the first curved path of the second portion has a steeper curvature compared to the second curved path of the second portion.

* * * * *